United States Patent
Yang et al.

(10) Patent No.: US 11,060,095 B2
(45) Date of Patent: *Jul. 13, 2021

(54) METHOD FOR ISOLATING CROSS-REACTIVE APTAMER AND USE THEREOF

(71) Applicants: Weijuan Yang, Miami, FL (US); Haixiang Yu, Miami, FL (US); Yingzhu Liu, Miami, FL (US); Yi Xiao, Miami, FL (US)

(72) Inventors: Weijuan Yang, Miami, FL (US); Haixiang Yu, Miami, FL (US); Yingzhu Liu, Miami, FL (US); Yi Xiao, Miami, FL (US)

(73) Assignee: THE FLORIDA INTERNATIONAL UNIVERSITY BOARD OF TRUSTEES, Miami, FL (US)

(\*) Notice: Subject to any disclaimer, the term of this patent is extended or adjusted under 35 U.S.C. 154(b) by 0 days.

This patent is subject to a terminal disclaimer.

(21) Appl. No.: 17/117,317

(22) Filed: Dec. 10, 2020

(65) Prior Publication Data

US 2021/0102210 A1    Apr. 8, 2021

Related U.S. Application Data

(60) Division of application No. 16/791,101, filed on Feb. 14, 2020, now Pat. No. 10,907,162, which is a continuation of application No. 16/174,764, filed on Oct. 30, 2018, now Pat. No. 10,655,132.

(51) Int. Cl.
| | |
|---|---|
| *C12N 15/11* | (2006.01) |
| *C12N 15/115* | (2010.01) |
| *A61K 31/167* | (2006.01) |
| *A61K 31/137* | (2006.01) |
| *G01N 27/26* | (2006.01) |

(52) U.S. Cl.
CPC .......... *C12N 15/115* (2013.01); *A61K 31/137* (2013.01); *A61K 31/167* (2013.01); *G01N 27/26* (2013.01)

(58) Field of Classification Search
CPC ............ C12Q 1/6825; C12Q 2525/205; C12N 15/115; C12N 2310/16
See application file for complete search history.

(56) References Cited

U.S. PATENT DOCUMENTS

| | | | |
|---|---|---|---|
| 2001/0046674 A1 | 11/2001 | Ellington | |
| 2010/0105053 A1* | 4/2010 | Cho | ..................... C12Q 1/6837 435/6.19 |

OTHER PUBLICATIONS

Stojanovic, Milan N., et al., "Aptamer-Based Colorimetric Probe for Cocaine." J. Am. Chem. Soc., 2002, 124: 9678-9679.
Yang, Kyung-Ae, et al., "In vitro selection and amplification protocols for isolation of aptameric sensors for small molecules." Methods, 2016, 106: 58-65.
Yu, Haixiang, et al., "In vitro isolation of small-molecule-binding aptamers with intrinsic dye-displacement functionality." Nucleic Acids Research, 2018, 46(8): e43, 1-9.

\* cited by examiner

*Primary Examiner* — Dana H Shin
(74) *Attorney, Agent, or Firm* — Saliwanchik, Lloyd & Eisenschenk

(57) ABSTRACT

The subject invention provides a SELEX strategy for isolating cross-reactive aptamers that recognize a core structure of a small-molecule family and bind to several structurally-similar molecules in the family. The subject invention also provides methods, assays, and products for detecting small-molecule targets of the family in a sample in both clinical and field settings. Such method is based on an aptamer sensor that reports the presence of small-molecule targets via a sensitive colorimetric signal for naked-eye detection. The subject invention further provides exonuclease-based methods for generating structure-switching aptamers from fully folded aptamers and developing electrochemical aptamer-based (E-AB) sensors for rapid and sensitive detection of synthetic cathinones.

20 Claims, 16 Drawing Sheets
(14 of 16 Drawing Sheet(s) Filed in Color)
Specification includes a Sequence Listing.

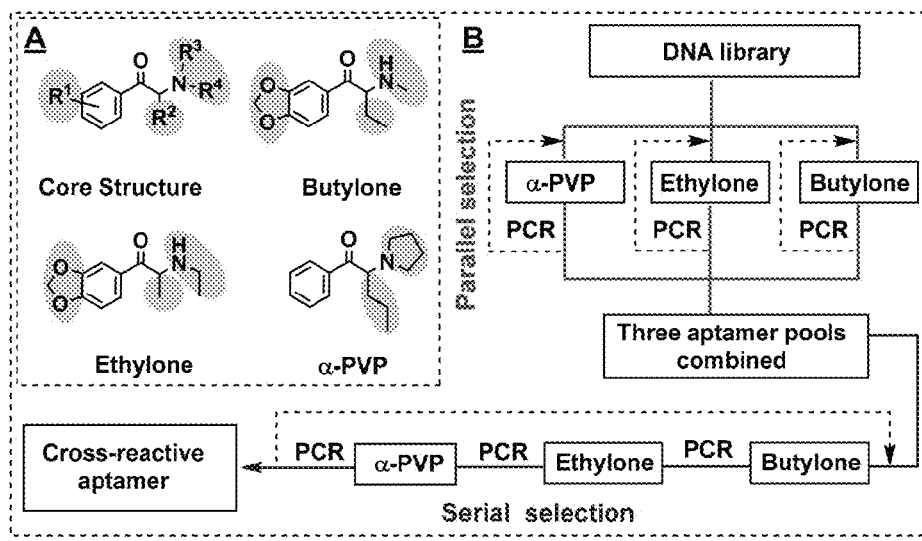
FIG. 1A    FIG. 1B
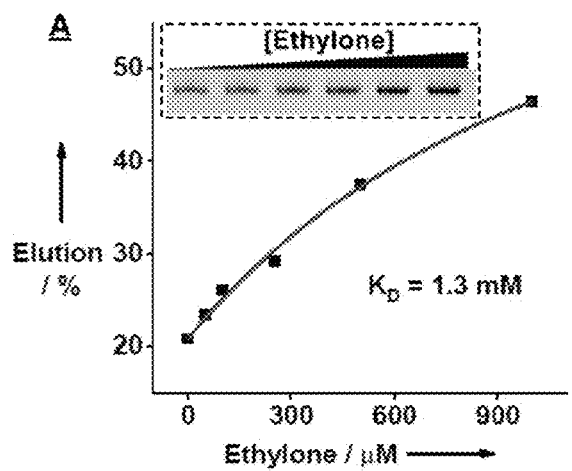    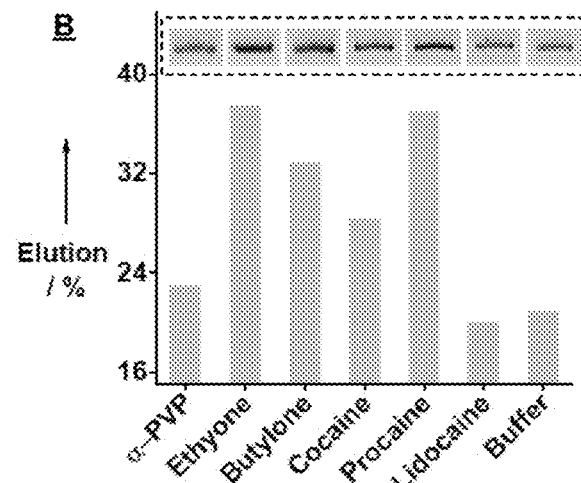
FIG. 2A    FIG. 2B

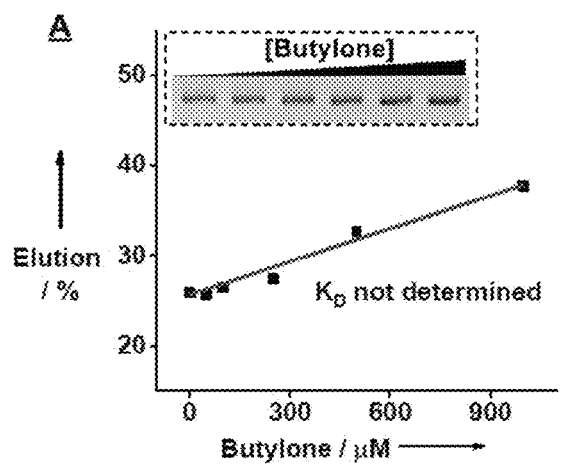
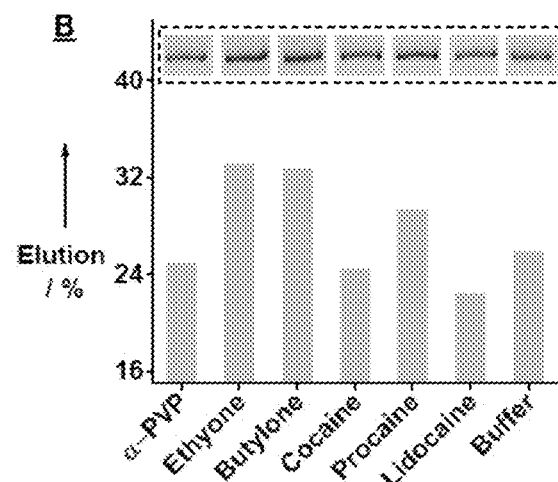
FIG. 3A
FIG. 3B
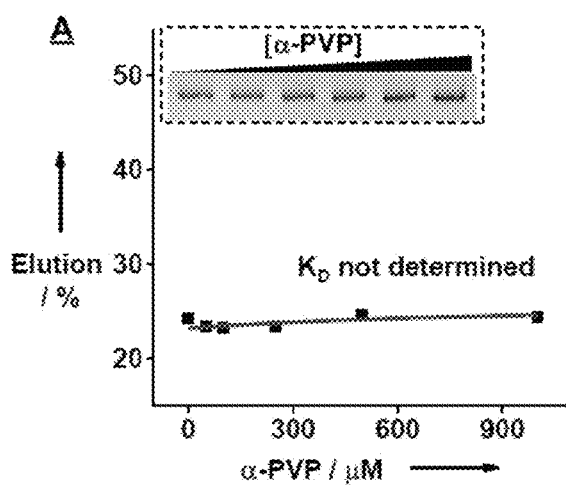
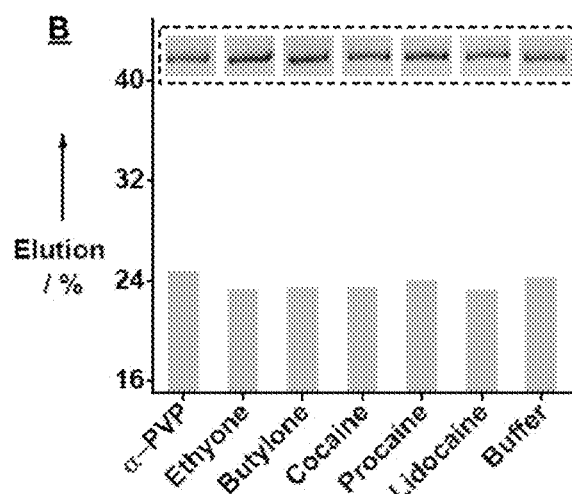
FIG. 4A
FIG. 4B

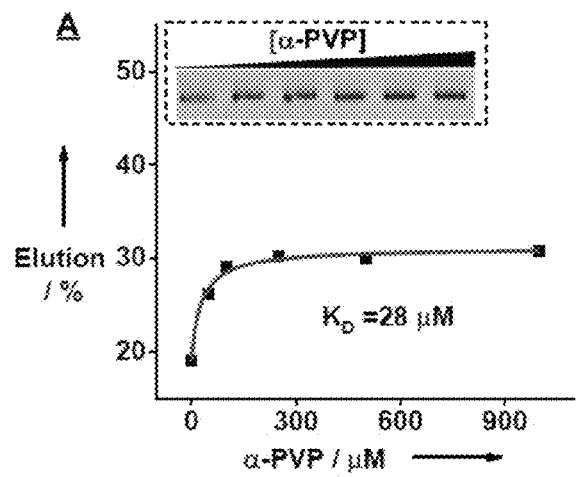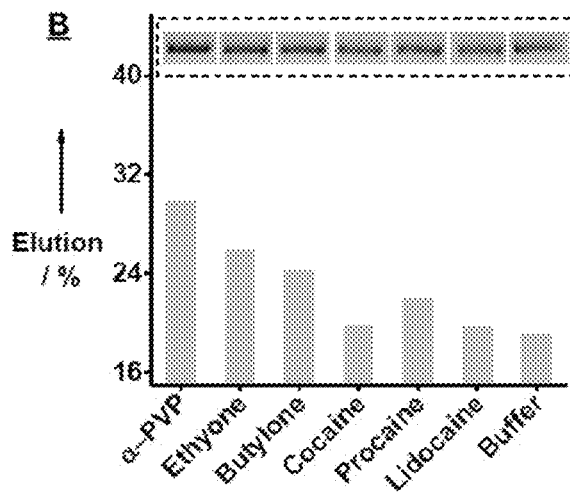
FIG. 5A
FIG. 5B
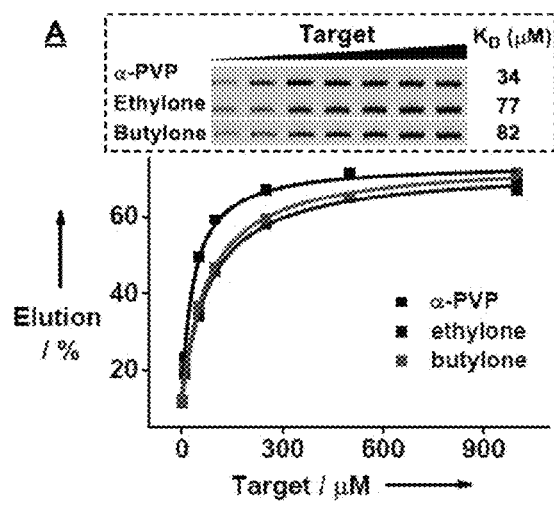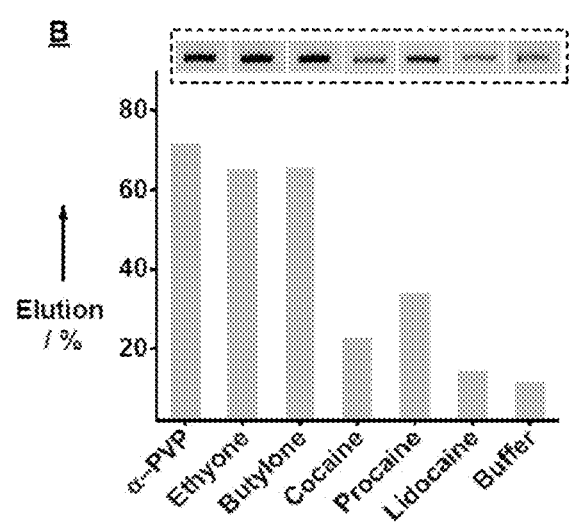
FIG. 6A
FIG. 6B

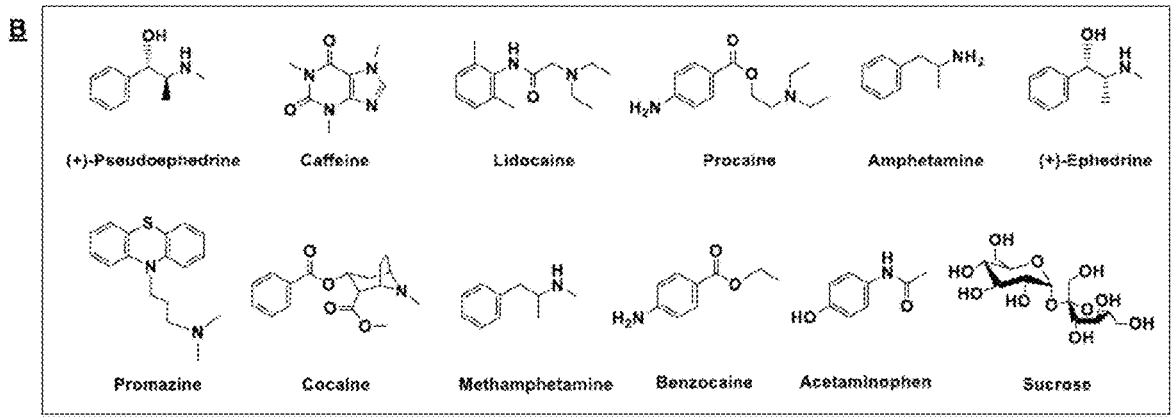

FIG. 8B

| Sequences (5' – 3') | Counts (total 50) | SEQ ID NO. |
|---|---|---|
| CTTAAGTGGGGTTCGGGTGGAGTTTATGGG | 30 | SEQ ID NO: 17 |
| TGAGAAGTGTGATTCAGTATGTTTTCCGAA | 7 | SEQ ID NO: 16 |
| CGAGAAGTGTGTTCAGTGAGTTTTCCGAGG | 4 | SEQ ID NO: 15 |
| CGCGGGGGTGGCTGGGGGTGTCTAGCAGAG | 2 | SEQ ID NO: 14 |
| ATTAAGTGGGGTTCGGGTGGAGTTTATGGG | 1 | SEQ ID NO: 13 |
| CCTTGGGTAGGTCAGTGTGGGGTTAGGGA | 1 | SEQ ID NO: 12 |
| CTTAAGTGGGGTTCGGGCGGAGTTTATGGG | 1 | SEQ ID NO: 11 |
| GGGAAGTGGGGTTCGGGTGGTGTTTTCCCA | 1 | SEQ ID NO: 10 |
| GGGATGGGGTGCTCGGTCGGGGGTTGTGAG | 1 | SEQ ID NO: 9 |
| GGTAAGAGTGGTTCCAGTTGAGTTTATGCC | 1 | SEQ ID NO: 8 |
| GGTCAGCACCTGTCGTGGTGGAGGGGTACT | 1 | SEQ ID NO: 7 |

FIG. 9

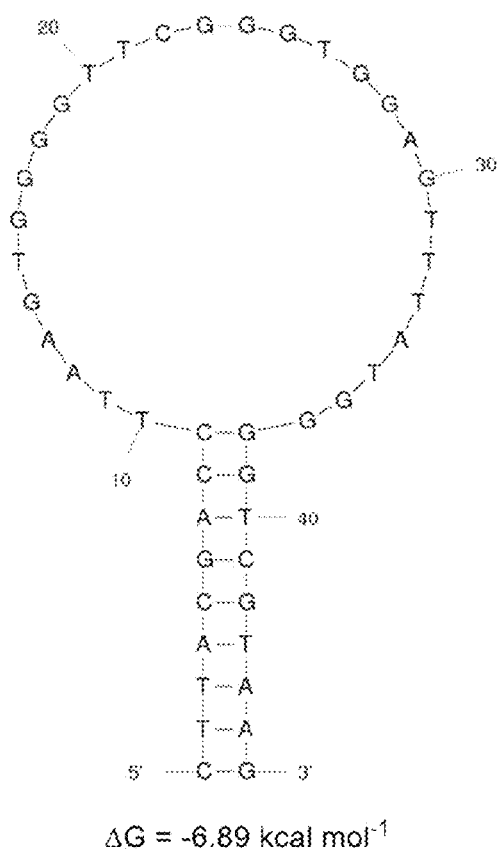
$\Delta G = -6.89$ kcal mol$^{-1}$
FIG. 10
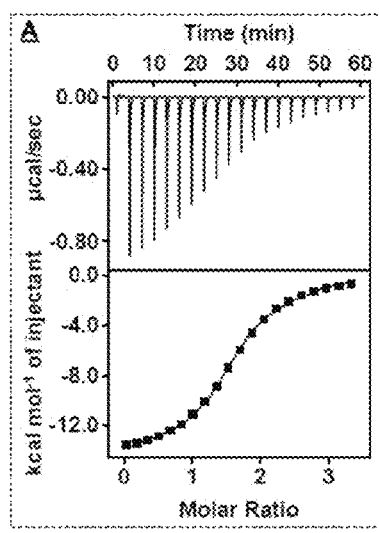 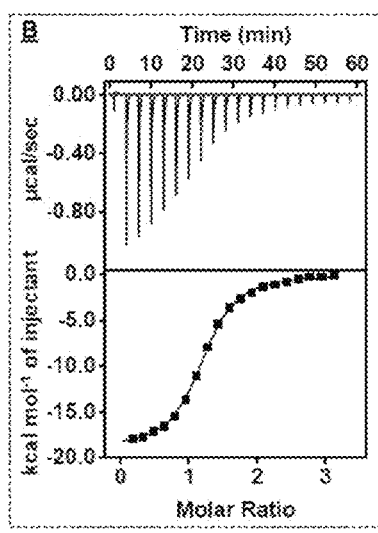 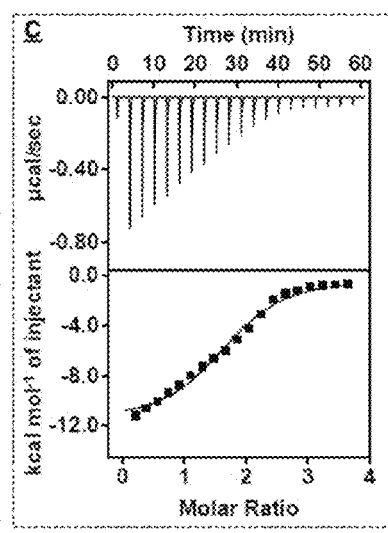
FIG. 11A        FIG. 11B        FIG. 11C

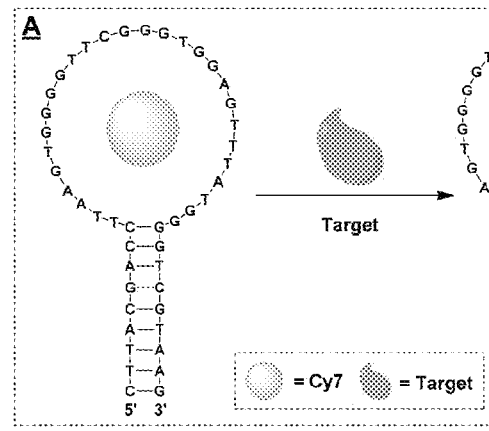
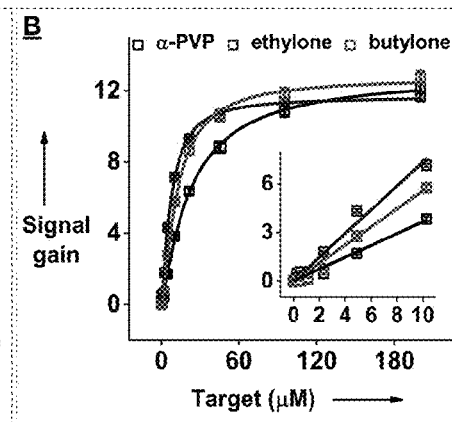
FIG. 12A
FIG. 12B
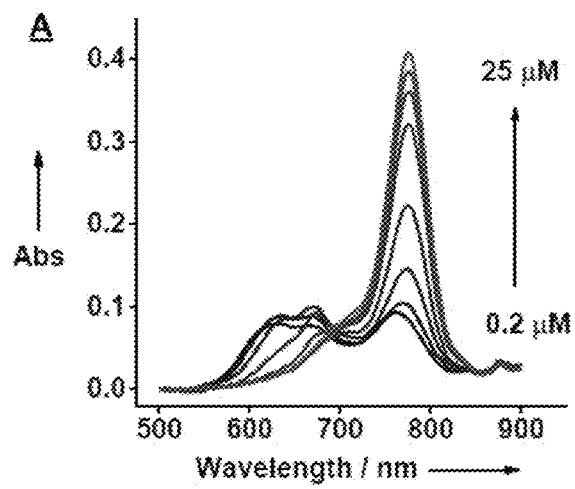
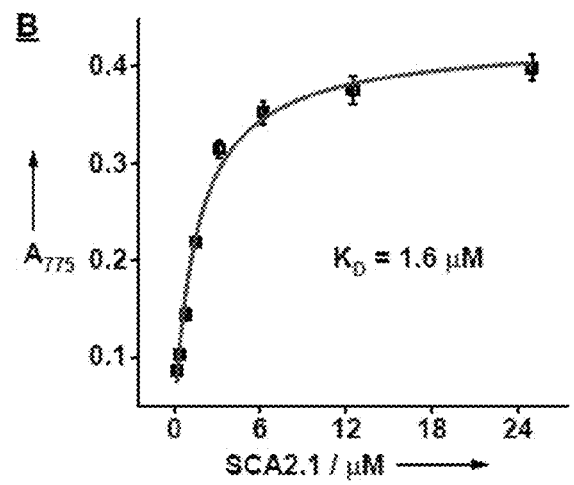
FIG. 13A
FIG. 13B

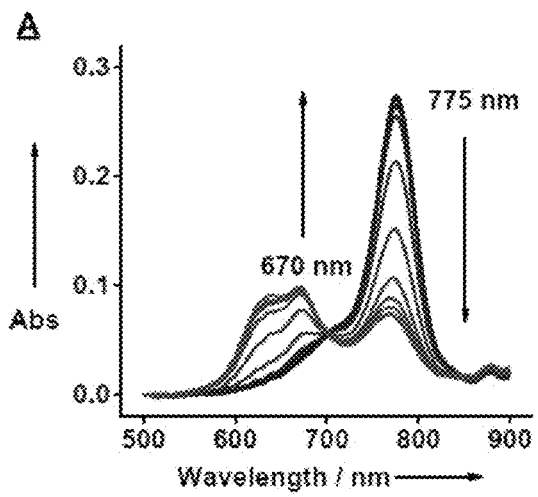
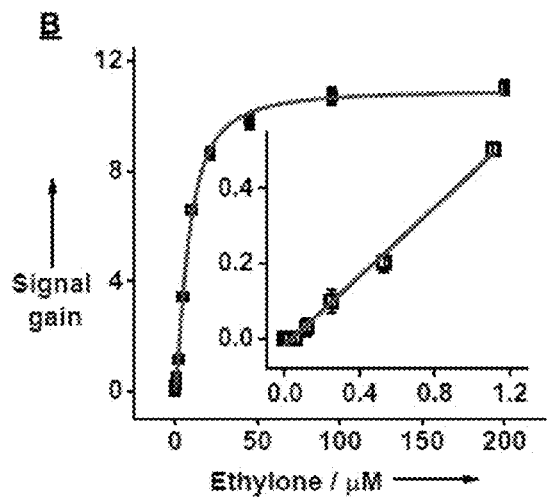
FIG. 16A
FIG. 16B
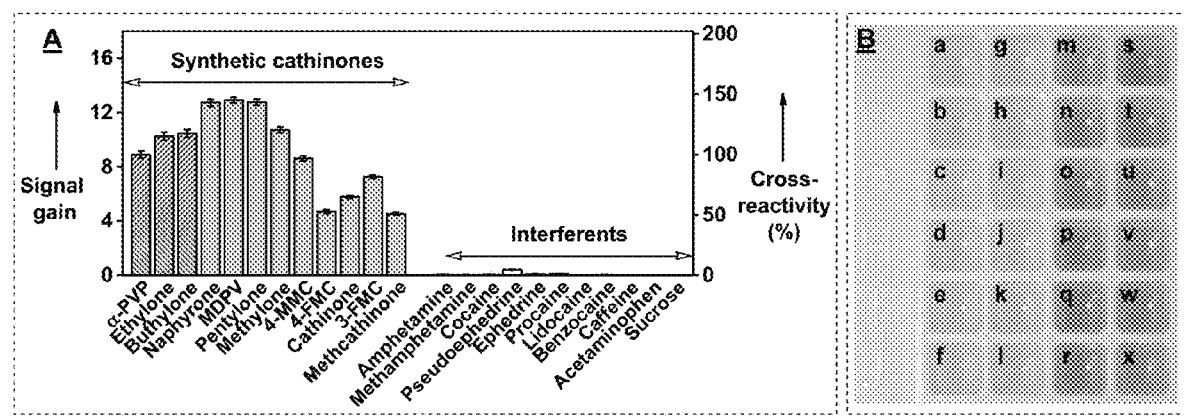
FIG. 17A
FIG. 17B

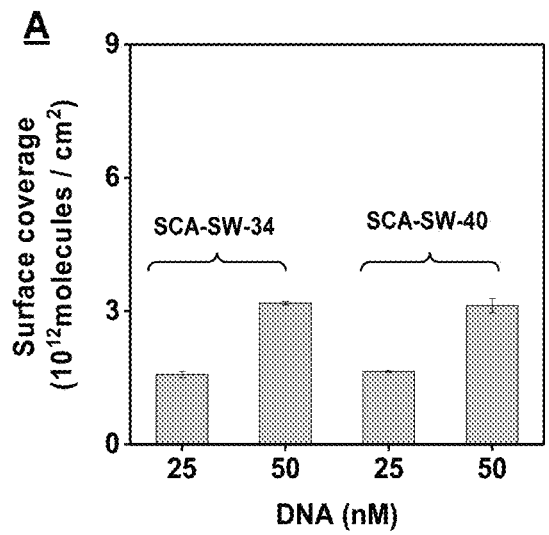
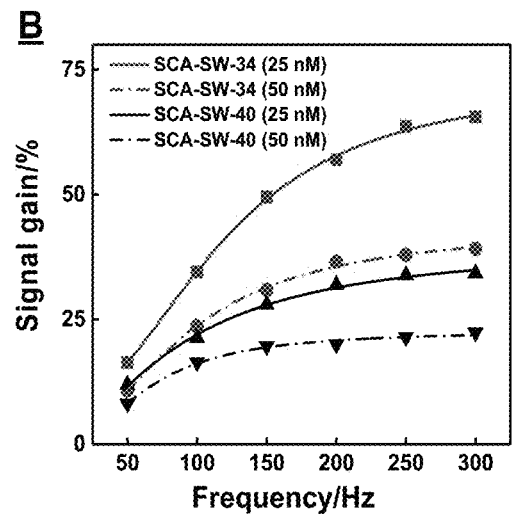
FIG. 26A
FIG. 26B
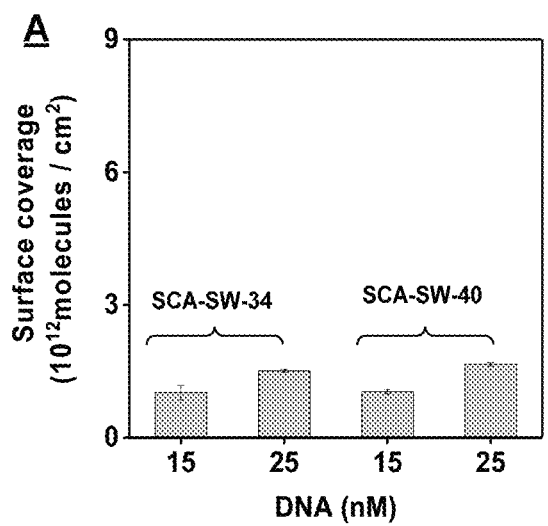
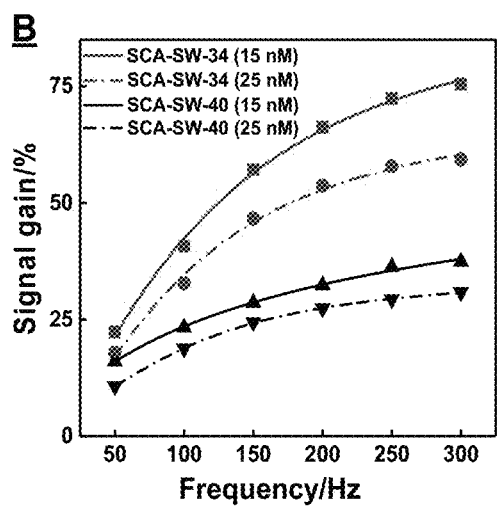
FIG. 27A
FIG. 27B

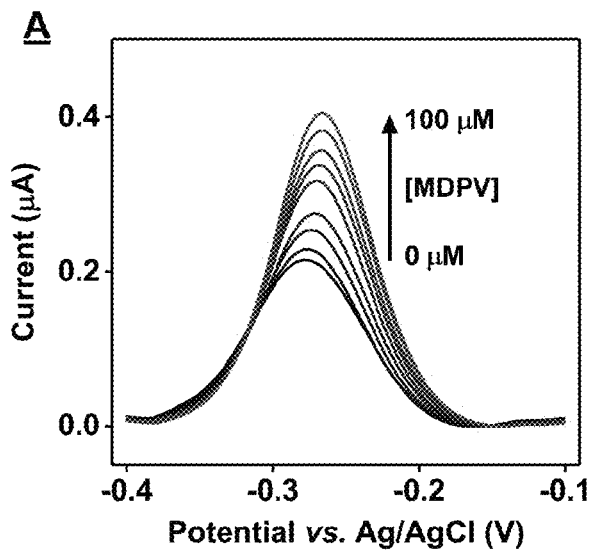
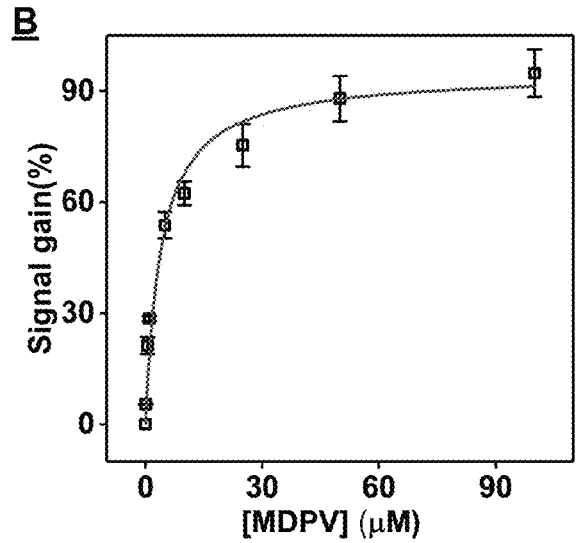
FIG. 28A           FIG. 28B
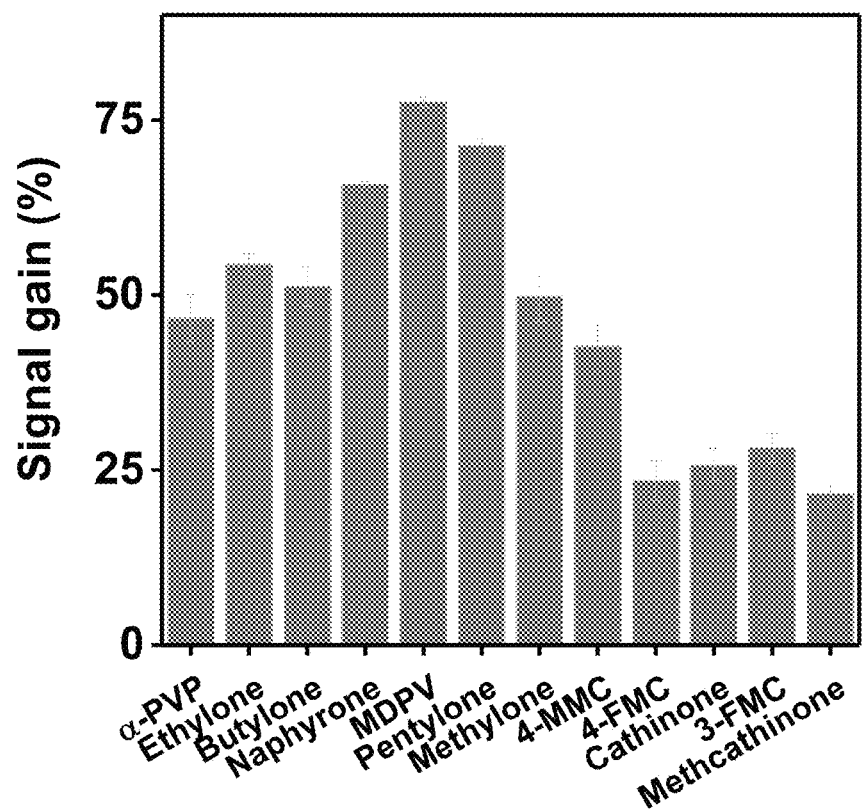
FIG. 29

SEQUENCE LISTING

```
<160> NUMBER OF SEQ ID NOS: 19

<210> SEQ ID NO 1
<211> LENGTH: 73
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (24)..(53)
<223> OTHER INFORMATION: n is a, c, g, or t

<400> SEQUENCE: 1
cgagcatagg cagaacttac gacnnnnnnn nnnnnnnnnn nnnnnnnnnn nnngtcgtaa     60
gagcgagtca ttc                                                        73

<210> SEQ ID NO 2
<211> LENGTH: 25
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (25)..(25)
<223> OTHER INFORMATION: biotin modification

<400> SEQUENCE: 2
tttttgtcgt aagttctgcc atttt                                           25

<210> SEQ ID NO 3
<211> LENGTH: 20
<212> TYPE: DNA
<213> ORGANISM: Artificial sequence
<220> FEATURE:
<223> OTHER INFORMATION: oligonucleotide
```

<400> SEQUENCE: 3
cgagcatagg cagaacttac                                              20

<210> SEQ ID NO 4
<211> LENGTH: 20
<212> TYPE: DNA
<213> ORGANISM: Artificial sequence
<220> FEATURE:
<223> OTHER INFORMATION: oligonucleotide
<220> FEATURE:
<221> NAME/KEY: misc_feature
<222> LOCATION: (1)..(1)
<223> OTHER INFORMATION: biotin modification

<400> SEQUENCE: 4
gaatgactcg ctcttacgac                                              20

<210> SEQ ID NO 5
<211> LENGTH: 20
<212> TYPE: DNA
<213> ORGANISM: Artificial sequence
<220> FEATURE:
<223> OTHER INFORMATION: oligonucleotide

<400> SEQUENCE: 5
gaatgactcg ctcttacgac                                              20

<210> SEQ ID NO 6
<211> LENGTH: 46
<212> TYPE: DNA
<213> ORGANISM: Artificial sequence
<220> FEATURE:
<223> OTHER INFORMATION: oligonucleotide

<400> SEQUENCE: 6
cttacgacct taagtggggt tcgggtggag tttatgggt cgtaag                  46

<210> SEQ ID NO 7
<211> LENGTH: 30
<212> TYPE: DNA
<213> ORGANISM: Artificial sequence
<220> FEATURE:
<223> OTHER INFORMATION: oligonucleotide

<400> SEQUENCE: 7
ggtcagcacc tgtcgtggtg gaggggtact                                   30

<210> SEQ ID NO 8
<211> LENGTH: 30
<212> TYPE: DNA
<213> ORGANISM: Artificial sequence
<220> FEATURE:
<223> OTHER INFORMATION: oligonucleotide

<400> SEQUENCE: 8
ggtaagagtg gttccagttg agtttatgcc                                   30

<210> SEQ ID NO 9
<211> LENGTH: 30
<212> TYPE: DNA
<213> ORGANISM: Artificial sequence
<220> FEATURE:
<223> OTHER INFORMATION: oligonucleotide

<400> SEQUENCE: 9
gggatggggt gctcggtcgg gggttgtgag                                   30

<210> SEQ ID NO 10
<211> LENGTH: 30
<212> TYPE: DNA
<213> ORGANISM: Artificial sequence
<220> FEATURE:
<223> OTHER INFORMATION: oligonucleotide

<400> SEQUENCE: 10
gggaagtggg gttcgggtgg tgttttccca                30

<210> SEQ ID NO 11
<211> LENGTH: 30
<212> TYPE: DNA
<213> ORGANISM: Artificial sequence
<220> FEATURE:
<223> OTHER INFORMATION: oligonucleotide

<400> SEQUENCE: 11
cttaagtggg gttcgggcgg agtttatggg                30

<210> SEQ ID NO 12
<211> LENGTH: 29
<212> TYPE: DNA
<213> ORGANISM: Artificial sequence
<220> FEATURE:
<223> OTHER INFORMATION: oligonucleotide

<400> SEQUENCE: 12
ccttgggtag gtcagtgtgg ggttaccca                 29

<210> SEQ ID NO 13
<211> LENGTH: 30
<212> TYPE: DNA
<213> ORGANISM: Artificial sequence
<220> FEATURE:
<223> OTHER INFORMATION: oligonucleotide

<400> SEQUENCE: 13
attaagtggg gttcgggtgg agtttatggg                30

<210> SEQ ID NO 14
<211> LENGTH: 30
<212> TYPE: DNA
<213> ORGANISM: Artificial sequence
<220> FEATURE:
<223> OTHER INFORMATION: oligonucleotide

<400> SEQUENCE: 14 cgcggggtg gctggggtg tctagcagag                  30

<210> SEQ ID NO 15
<211> LENGTH: 30
<212> TYPE: DNA
<213> ORGANISM: Artificial sequence
<220> FEATURE:
<223> OTHER INFORMATION: oligonucleotide

<400> SEQUENCE: 15
cgagaagtgt gttcagtgag ttttccgagg                30

<210> SEQ ID NO 16
<211> LENGTH: 30
<212> TYPE: DNA
<213> ORGANISM: Artificial sequence
<220> FEATURE:

```
<223> OTHER INFORMATION: oligonucleotide

<400> SEQUENCE: 16
tgagaagtgt gattcagtat gttttccgaa                                          30

<210> SEQ ID NO 17
<211> LENGTH: 30
<212> TYPE: DNA
<213> ORGANISM: Artificial sequence
<220> FEATURE:
<223> OTHER INFORMATION: oligonucleotide

<400> SEQUENCE: 17
cttaagtggg gttcgggtgg agtttatggg                                          30

<210> SEQ ID NO 18
<211> LENGTH: 40
<212> TYPE: DNA
<213> ORGANISM: Artificial sequence
<220> FEATURE:
<223> OTHER INFORMATION: oligonucleotide

<400> SEQUENCE: 18
cttacgacct taagtggggt tcgggtggag tttatggggt                               40

<210> SEQ ID NO 19
<211> LENGTH: 34
<212> TYPE: DNA
<213> ORGANISM: Artificial sequence
<220> FEATURE:
<223> OTHER INFORMATION: oligonucleotide

<400> SEQUENCE: 19
accttaagtg gggttcgggt ggagtttatg gggt                                     34
```

METHOD FOR ISOLATING CROSS-REACTIVE APTAMER AND USE THEREOF

CROSS-REFERENCE TO A RELATED APPLICATION

This application is a divisional application of co-pending U.S. Serial application Ser. No. 16/791,101, filed Feb. 14, 2020; which is a continuation application of U.S. Serial application Ser. No. 16/174,764, filed Oct. 30, 2018, now U.S. Pat. No. 10,655,132; all of which are incorporated herein by reference in their entirety.

GOVERNMENT SUPPORT

This invention was made with government support under 2016-DN-BX-0167 awarded by the National Institute of Justice. The government has certain rights in the invention.

SEQUENCE LISTING

The Sequence Listing for this application is labeled "SeqList-28Jun19-ST25.txt," which was created on Jun. 28, 2019, and is 5 KB. The Sequence Listing is incorporated herein by reference in its entirety.

BACKGROUND OF THE INVENTION

Small molecules are important targets with the potential of clinical or commercial applications such as medical diagnostics, environmental monitoring, and forensic science. Thus, efforts to develop methods for portable, low-cost, point-of-care and quantitative detection of a broad range of small molecules are gaining momentum.

Synthetic cathinones (also known as bath salts) are designer drugs sharing a similar core structure with amphetamines and 3, 4-methylenedioxy-methamphetamine (MDMA). They are highly addictive central nervous system stimulants, and are associated with many negative health consequences, including even death. Although these drugs have emerged only recently, abuse of bath salts has become a threat to public health and safety due to their severe toxicity, increasingly broad availability, and difficulty of regulation. More importantly, there is currently no reliable presumptive test for any synthetic cathinone. Chemical spot tests used to detect conventional drugs such as cocaine, methamphetamine, and opioids show no cross-reactivity to synthetic cathinones.

Screening for small molecules such as synthetic cathinones requires cross-reactive assays that can broadly detect small molecules based on their shared molecular framework. Such assays are more efficient and cost-effective than the tandem use of multiple highly specific assays that detect a single analyte.

Antibody-based immunoassays have dominated the field of on-site small-molecule detection, and while numerous assays have been developed for a variety of individual targets, the development of cross-reactive immunoassays has proven difficult. This is in part because the process of antibody generation, which is entirely in vivo, provides no control over the cross-reactivity of the generated antibody.

Nucleic acid-based bioaffinity elements known as aptamers hold much promise in overcoming many of the shortcomings associated with immunoassays. Aptamers are isolated through a process known as systematic evolution of ligands by exponential enrichment (SELEX) to bind targets of interest with high affinity and specificity. Aptamers can be isolated for essentially any target, including metal ions, small molecules, proteins, or whole cells.

Unlike antibodies, aptamers can be isolated relatively quickly and chemically synthesized in an inexpensive manner with no batch-to-batch variation. Aptamers are chemically stable and have shelf-lives of a few years at room temperature. Moreover, aptamers can be engineered to have tunable target-binding affinities or various functionalities. These advantages make aptamers ideal for use in biosensors.

Because SELEX is an in vitro process, it should be possible to isolate a cross-reactive aptamer through precise control of the selection strategy and conditions. Ideally, such aptamer should bind to the core structure of a given class of targets while being insensitive to peripheral substituents, thereby capable of recognizing the whole target family. However, little work has been done to demonstrate the capability of SELEX to achieve such goal.

Therefore, there is a need for developing a novel SELEX strategy to isolate cross-reactive aptamers for structurally-similar compounds. There are also needs for methods and materials for rapid, sensitive, on-site, and naked-eye detection of small molecules such as synthetic cathinones.

BRIEF SUMMARY OF THE INVENTION

The subject invention provides a novel SELEX strategy for isolating cross-reactive aptamers that recognize a core structure of a small-molecule family and bind each structurally-similar molecule in said family.

In one embodiment, the method employs a parallel-and-serial SELEX strategy, comprising at least one step of a parallel selection and at least one step of a serial selection. In another embodiment, the method for isolating an aptamer for a family of structurally-similar small molecules comprises mixing the small molecules in said family with a nucleic acid library, binding the small molecules to one or more aptamers in the nucleic acid library, separating the aptamer bound to the small molecules in said family from at least a portion of the unbound nucleic acid molecules, isolating the aptamer and optionally, amplifying the isolated aptamer.

In one embodiment, the aptamer isolated by the method according to the subject invention is a cross-reactive aptamer that recognizes and binds to the core structure of synthetic cathinones. The synthetic cathinones include, but are not limited to MDPV, ethylone, naphyrone, penthylone, methylone, buthylone, MPHP, 4-MMC, methedrone, pyrovalenrone, MDPBP, α-PVP, MEPBP, 4-FMC, and methcathinone. The aptamer does not cross-react with common cutting agents found in seized samples such as pseudoephedrine, promazine, procaine, ephedrine, acetaminophen, methamphetamine, lidocaine, amphetamine, cocaine, sucrose, and caffeine.

In one embodiment, the cross-reactive aptamer, according to the subjection, is a DNA aptamer comprising at least 46 nucleotides. The target-binding domain of the cross-reactive aptamer comprises a nucleotide sequence selected from SEQ ID Nos: 7-17 and sequences sharing at least 50%, 55%, 60%, 65%, 70%, 75%, 80%, 85%, 90%, 95%, 96%, 97%, 98% or 99% identity with SEQ ID Nos: 7-17. In a specific embodiment, the cross-reactive aptamer comprises a nucleotide sequence of SCA2.1 (SEQ ID NO: 6). In a preferred embodiment, the cross-reactive aptamer is SCA2.1 (SEQ ID NO: 6) and sequences sharing at least 50%, 55%, 60%, 65%, 70%, 75%, 80%, 85%, 90%, 95%, 96%, 97%, 98% or 99% identity with SCA2.1 (SEQ ID NO: 6).

The subject invention provides methods, assays, and products for rapid, naked-eye detection of small molecules in a sample, in particular, in both clinical and field settings. The subject invention is based on an aptamer sensor that reports the presence of small-molecule targets such as synthetic cathinones via a sensitive colorimetric signal for naked-eye detection. Specifically, exemplified herein is a method for detecting synthetic cathinones in bodily fluids, drinks, and/or seized substances.

In one embodiment, the subject invention provides a method for generating cross-reactive aptamers with structure-switching functionality and a means of rapid and sensitive detection of a small-molecule target family. The generation of a structure-switching cross-reactive aptamer entails digesting the cross-reactive aptamer with an exonuclease mixture, such as exonuclease III (Exo III) and exonuclease I (Exo I). The resulting digestion product has structure-switching functionality with similar or equal affinity as its parent cross-reactive aptamer, and such structure-switching cross-reactive aptamer can be directly employed in folding-based aptamer sensors.

In some embodiments, the cross-reactive aptamers with structure-switching functionality are fragments of the cross-reactive aptamers. In specific embodiments, the structure-switching cross-reactive aptamer comprises a nucleotide sequence of SCA-SW-40 (SEQ ID NO: 18) or SCA-SW-34 (SEQ ID NO: 19). Preferably, the structure-switching cross-reactive aptamer is SCA-SW-40 (SEQ ID NO: 18), SCA-SW-34 (SEQ ID NO: 19) or sequences sharing at least 50%, 55%, 60%, 65%, 70%, 75%, 80%, 85%, 90%, 95% or 99% identity with SCA-SW-40 (SEQ ID NO: 18) or SCA-SW-34 (SEQ ID NO: 19).

In one embodiment, the subject invention provides a method for detecting a small molecule target or a small-molecule target family in a sample using the structure-switching cross-reactive aptamer.

In one embodiment, the subject invention provides methods for rapid and sensitive detection of a small-molecule target or a small-molecule target family in a sample by incorporating the structure-switching cross-reactive aptamers into an electrochemical aptamer-based (E-AB) sensor, which has demonstrated target-induced conformational changes within the aptamers and has achieved excellent sensor performance. The method comprises contacting the sample with the E-AB sensor, and detecting the small-molecule target/target family in the sample, wherein the detection comprises measuring a signal generated from a signal reporter.

In one embodiment, the subject invention provides a kit suitable for screening aptamers that bind to a family of structurally similar molecules of interest. The kit comprises a suitable container, an oligonucleotide library, and instructions for use in performing a screen for aptamers that bind to the family of structurally similar molecules of interest. The kit may optionally further comprise one or more reagents, one or more suitable primers and enzymes, e.g., nucleases, and one or more buffers.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

FIGS. 1A-1B show the isolation of a cross-reactive aptamer binding to synthetic cathinones using a parallel-and-serial SELEX strategy. (1A) The core structure of synthetic cathinones and the three targets chosen for parallel-and-serial SELEX. The substituent moieties on the beta-keto phenethylamine core structure are shaded in red. (1B) The schematic diagram of parallel-and-serial SELEX.

FIGS. 2A-2B show the determination of the target-binding affinity, cross-reactivity, and specificity of the round P5 ethylone pool via a gel elution assay. (2A) Polyacrylamide gel electrophoresis (PAGE) results depict the target elution profile with lanes representing samples of the pool eluted with 0, 50, 100, 250, 500, or 1000 µM ethylone (from left to right). The percent of target-eluted pool was plotted against the concentration of ethylone employed for elution to determine the binding affinity of the enriched pool. (2B) PAGE results of enriched pool eluted with 500 µM synthetic cathinones (α-PVP, ethylone, and butylone) or interferents (cocaine, procaine, and lidocaine) was used to measure target-cross-reactivity and specificity of the enriched pool.

FIGS. 3A-3B show the determination of the target-binding affinity, cross-reactivity, and specificity of the round P5 butylone pool via a gel elution assay. (3A) Polyacrylamide gel electrophoresis (PAGE) results depict the target elution profile with lanes representing samples of the pool eluted with 0, 50, 100, 250, 500, or 1000 µM butylone (from left to right). The percent of target-eluted pool was plotted against the concentration of butylone employed for elution to determine the binding affinity of the enriched pool. (3B) PAGE results of enriched pool eluted with 500 µM synthetic cathinones (α-PVP, ethylone, and butylone) or interferents (cocaine, procaine, and lidocaine) was used to measure target-cross-reactivity and specificity of the enriched pool.

FIGS. 4A-4B show the determination of the target-binding affinity, cross-reactivity, and specificity of the round P5 α-PVP pool via a gel elution assay. (4A) Polyacrylamide gel electrophoresis (PAGE) results depict the target elution profile with lanes representing samples of the pool eluted with 0, 50, 100, 250, 500, or 1000 µM α-PVP (from left to right). The percent of target-eluted pool was plotted against the concentration of α-PVP employed for elution to determine the binding affinity of the enriched pool. (4B) PAGE results of enriched pool eluted with 500 µM synthetic cathinones (α-PVP, ethylone, and butylone) or interferents (cocaine, procaine, and lidocaine) was used to measure target-cross-reactivity and specificity of the enriched pool.

FIGS. 5A-5B show the determination of the target-binding affinity, cross-reactivity, and specificity of the round P9 α-PVP pool via a gel elution assay. (5A) Polyacrylamide gel electrophoresis (PAGE) results depict the target elution profile with lanes representing samples of the pool eluted with 0, 50, 100, 250, 500, or 1000 µM α-PVP (from left to right). The percent of target-eluted pool was plotted against the concentration of α-PVP employed for elution to determine the binding affinity of the enriched pool. (5B) PAGE results of enriched pool eluted with 500 µM synthetic cathinones (α-PVP, ethylone, and butylone) or interferents (cocaine, procaine, and lidocaine) was used to measure target-cross-reactivity and specificity of the enriched pool.

FIGS. 6A-6B show the determination of the target-binding affinity, cross-reactivity and specificity of the round S3 pool via a gel elution assay. (6A) PAGE results depict the target elution profile with lanes representing samples of the pool eluted with 0, 10, 50, 100, 250, 500, or 1000 µM (from left to right) of α-PVP, ethylone, or butylone. The percent of target-eluted pool was plotted against the concentration of target used for elution to determine the binding affinity of the enriched pool. (6B) PAGE results of enriched pool eluted with 500 µM synthetic cathinones (α-PVP, ethylone, and butylone) or interferents (cocaine, procaine, and lidocaine) was used to measure target-cross-reactivity and specificity of the enriched pool.

FIGS. 8A-8B show the chemical structures of the (8A) synthetic cathinones and (8B) interferent compounds studied in this work.

FIG. 9 shows the sequences of randomized region of oligonucleotides from the final enriched pool after trimming and alignment by BioEdit software. Sequences (SEQ ID NOs: 7-17) are oligonucleotides in the randomized region. The prevalence of each oligonucleotide is ranked from highest (top) to lowest (bottom) using the frequency of appearance (count) as a benchmark. SEQ ID NO: 17 is the oligonucleotide sequence of the randomized region of the SCA2.1 aptamer. SEQ ID NO: 16 is the oligonucleotide sequence of the randomized region of the SCA1.1 aptamer. SEQ ID NO: 15 is the oligonucleotide sequence of the randomized region of the SCA1.2 aptamer.

FIG. 10 shows the secondary structure of SCA2.1 (SEQ ID NO: 6) as predicted by Mfold under the selection ion concentrations (20 mM NaCl and 0.5 mM $MgCl_2$) at 23° C. The estimated free energy of formation is shown below.

FIGS. 11A-11C show the characterization of the target-binding affinity of SCA2.1 using isothermal titration calorimetry. Top panels present raw data showing the heat generated from each titration of (11A) butylone, (11B) ethylone and (11C) α-PVP to SCA2.1, while bottom panels show the integrated heat of each titration after correcting for dilution heat of the titrant.

FIGS. 12A-12B show the colorimetric detection of synthetic cathinones using a Cy7-displacement assay. (12A) Schematic of the Cy7-displacement assay, wherein binding of a synthetic cathinone molecule displaces Cy7 monomer from the binding domain of SCA2.1 (SEQ ID NO: 6), thus inducing formation of Cy7 dimer that produces a change in the absorbance of the dye. (12B) Calibration curves based on the absorbance ratio at 670/775 nm in the presence of different concentrations of α-PVP, ethylone or butylone (0, 0.1, 0.3, 0.5, 1.1, 2.3, 4.9, 10.3, 21.6, 45.4, 95.2, 200 µM). The inset represents the linear range at 0 to 10 µM target. Error bars show standard deviation from three measurements at each concentration. [SCA 2.1]=3 µM, [Cy7]=2 µM.

FIGS. 13A-13B show the determination of the binding affinity of Cy7 to SCA2.1 via a colorimetric assay. (13A) Absorbance spectra of 2 µM Cy7 in the presence of varying concentrations of SCA2.1 (0.2, 0.4, 0.8, 1.6, 3.1, 6.3, 12.5, or 25 µM), with the black-to-red color gradient representing increasing concentrations of SCA2.1. (13B) The plot of the absorbance of Cy7 monomer at its peak wavelength (775 nm) versus concentration of SCA2.1 was fitted with the Langmuir equation to determine the binding affinity of Cy7 to SCA2.1.

FIG. 16A-16B show the detection of ethylone in 50% saliva using the SCA2.1-based Cy7-displacement colorimetric assay. (16A) Absorbance spectra of Cy7 (2 µM) in the presence of varying concentrations of ethylone (0, 0.03, 0.06, 0.12, 0.25, 0.53, 1.11, 2.33, 4.90, 10.28, 21.60, 45.35, 95.24, 200 µM), with the black-to-red color gradient representing increasing concentrations of synthetic cathinone target. (16B) Assay calibration curve generated using 0-200 µM ethylone with the inset representing linear range from 0 to 1.2 µM target. [SCA2.1]=3 µM.

FIGS. 17A-17B show the colorimetric detection of synthetic cathinones using a Cy7-displacement assay. (17A) Signal gain measured via an instrument from the Cy7-displacement assay with 12 synthetic cathinones (gray, the three selection targets are shaded) and 11 common interferents (white) at a concentration of 50 µM with 3 µM SCA2.1 and 2 µM Cy7. Error bars show standard deviations from three measurements of each compound. (17B) Naked-eye detection of synthetic cathinones using a mixture of 5 µM of SCA2.1 and 3.5 µM Cy7. The solution appears as a faint blue color in the absence of target and 50 µM interferents (17B, a-i). However, the color of the solutions changes to bright blue within seconds upon addition of 50 µM synthetic cathinones (17B, m-x).

FIGS. 26A-26B show the effect of 5'-overhang on E-AB sensor performance. (26A) Determination of aptamer surface coverage on gold electrodes modified with either 25 or 50 nM of SCA-SW-34 or SCA-SW-40. (26B) Effect of frequency on signal gain using 30 MDPV with SCA-SW-34 or SCA-SW-40 modified electrodes. Error bars shown are standard error for the mean of measurements using three separate electrodes. Experiments were performed in selection buffer (10 mM Tris-HCl (pH 7.4), 20 mM NaCl, 0.5 mM $MgCl_2$).

FIGS. 27A-27B show the effect of 5'-overhang on E-AB sensor performance. (27A) Determination of aptamer surface coverage on gold electrodes modified with either 15 or 25 nM of SCA-SW-34 or SCA-SW-40. (27B) Effect of frequency on signal gain using 30 MDPV with SCA-SW-34 or SCA-SW-40 modified electrodes. Error bars shown are standard error for the mean of measurements using three separate electrodes. Experiments were performed in selection buffer (10 mM Tris-HCl (pH 7.4), 20 mM NaCl, 0.5 mM $MgCl_2$).

FIGS. 28A-28B show sensitive MDPV detection using optimized conditions (10 mM Tris-HCl (pH 7.4), 0.1 mM NaCl, 0.03 mM $MgCl_2$). (A) E-AB sensor response to various concentrations of MDPV (0, 0.1, 0.5, 1, 5, 10, 25, 50 and 100 µM). (B) Calibration curve of MDPV detection. Error bars shown are standard error for the mean of measurements using three separate electrodes.

FIG. 29 shows the cross-reactivity of the E-AB sensor against various synthetic cathinones at a concentration of 25 µM under optimized buffer conditions.

BRIEF DESCRIPTION OF SEQUENCES

Figures 7A, 7B:
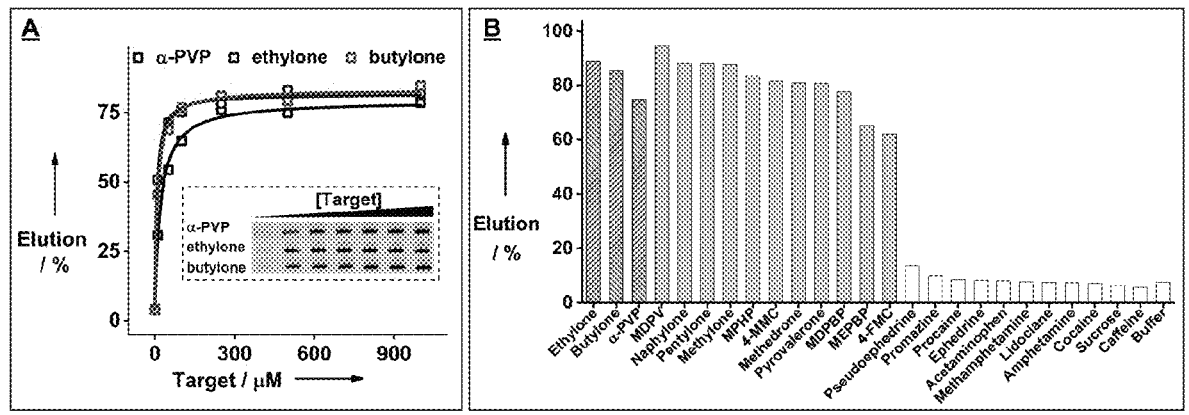
FIGS. 7A-7B show the determination of the target-binding affinity, cross-reactivity, and specificity of the final enriched pool via a gel elution assay. (7A) PAGE results depict the target elution profile with lanes representing samples of the pool eluted with 0, 10, 50, 100, 250, 500, or 1000 µM (from left to right) α-PVP, ethylone, or butylone. The percent of target-eluted pool was plotted against the concentration of target to determine the binding affinity of the enriched pool. (7B) Percent elution values were reported for 16 synthetic cathinones and 11 interferents at a concentration of 50 µM.

SEQ ID NO: 1 is the DNA sequence of a library contemplated for use according to the subject invention, where N is a random base.

SEQ ID NO: 2 is the sequence of a biotinylated cDNA contemplated for use according to the subject invention.

SEQ ID NO: 3 is the sequence of a forward primer contemplated for use according to the subject invention.

SEQ ID NO: 4 is the sequence of a biotinylated reverse primer contemplated for use according to the subject invention.

SEQ ID NO: 5 is the sequence of a reverse primer contemplated for use according to the subject invention.

SEQ ID NO: 6 is the DNA sequence of SCA2.1 contemplated for use according to the subject invention.

SEQ ID NOs: 7-17 are the DNA sequences of radomized regions of cross-reactive aptamers contemplated for use according to the subject invention.

SEQ ID NO: 18 is the DNA sequence of SCA-SW-40 contemplated for use according to the subject invention.

SEQ ID NO: 19 is the DNA sequence of SCA-SW-34 contemplated for use according to the subject invention.

DETAILED DESCRIPTION OF THE INVENTION

The subject invention provides a novel SELEX strategy for isolating cross-reactive aptamers that recognize a core structure of a small-molecule family and bind to structurally-similar molecules in said family. The subject invention also provides methods, assays, and products for rapid, naked-eye detection of small molecules in a sample, in particular, in both clinical and field settings.

In one embodiment, the sample is a biological sample of a subject. In specific embodiments, the biological sample is selected from blood, plasma, urine, tears, sweat, and saliva. The subject may be any animal or human, preferably, a human. The subject may also be any animal including, but not limited to, non-human primates, rodents, dogs, cats, horses, cattle, pigs, sheep, goats, chickens, guinea pigs, hamsters and the like.

In one embodiment, the sample is an environmental sample, for example, water, soil, air, or plant sample. In another embodiment, the sample is a seized drug sample, for instance, a street drug sample seized by law enforcement or government officials.

Small Molecules

The term "target," "small molecule," or "small-molecule target," as used herein, includes any molecule capable of being detected using an aptamer technique. In certain embodiments, the small molecule has a molecular weight less than 1000 Daltons, less than 900 Daltons, less than 800 Daltons, less than 700 Daltons, less than 600 Daltons, less than 500 Daltons, less than 400 Daltons, less than 300 Daltons, or less than 200 Daltons.

In specific embodiments, the small-molecule target may be an amino acid, an amino acid-related molecule, a peptide, a steroid, a lipid, a sugar, a carbohydrate, a biomarker, a drug molecule, a drug metabolite, a coenzyme, a nucleotide (nt), a nucleotide-related molecule, a pyridine nucleotide, a cyclic nucleotide, or a cyclic dinucleotide. In other embodiments, the small-molecule target may be an infective agent, antigen, toxin, disease biomarker, or a specific metal ion.

In one embodiment, the small molecule is a drug molecule. In one embodiment, the drug molecule is a cathinone, a cathinone derivative, or synthetic cathinone, such as a ring-substituted cathinone derivative or synthetic cathinone. The synthetic cathinone has a general structure of formula (I)

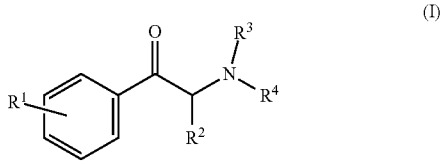

wherein $R^1$ $R^2$, $R^3$ and $R^4$, are each independently selected from the group consisting of hydrogen, alkyl, substituted alkyl, aryl, substituted aryl, benzyl, heteroaryl, substituted heteroaryl, cycloalkyl, substituted cycloalkyl, cycloalkenyl, substituted cycloalkenyl, heterocycloalkyl, alkenyl, alkynyl, alkoxy, thiol, haloalkyl, acyl, halogen, amino, alkylamino, hydroxyl, hydroxylalkyl, and —COOH.

In one embodiment, $R^1$ is selected from the group consisting of hydrogen, alkyl, aryl, heteroaryl, cycloalkyl, cycloalkenyl, heterocycloalkyl, alkenyl, alkynyl, haloalkyl, acyl, alkoxy, halogen, and hydroxylalkyl; $R^2$ is hydrogen or alkyl; and $R^3$ and $R^4$ are each independently selected from the group consisting of hydrogen, alkyl, aryl, heteroaryl, cycloalkyl, cycloalkenyl, heterocycloalkyl, alkenyl, alkynyl, haloalkyl, acyl, halogen, and hydroxylalkyl.

In a further embodiment, $R^1$ is halogen, such as fluorine, chlorine, bromine or iodine.

In some embodiments, $R^1$, taken together with the carbon atom to which it is attached and an adjacent carbon atom thereof, form a substituted or unsubstituted 5- or 6-membered homocyclic or heterocyclic ring. For example, $R^1$ may form a methylenedioxy group or aromatic ring such as benzene with two adjacent carbon atoms of the ring where it is attached.

In other embodiments, $R^3$ and $R^4$, taken together with the nitrogen atom to which they are attached, form a substituted or unsubstituted 5- or 6-membered heterocyclic ring. For example, $R^3$ and $R^4$ may form a pyrrolidino group.

As used herein, "alkyl" means linear saturated monovalent radicals of at least one carbon atom or a branched saturated monovalent of at least three carbon atoms. It may include hydrocarbon radicals of at least one carbon atom, which may be linear. Examples include, but are not limited to, methyl, ethyl, propyl, 2-propyl, n-butyl, iso-butyl, tert-butyl, pentyl, hexyl, and the like.

As used herein, "acyl" means a radical —C(O)R where R includes, but is not limited to, hydrogen, alkyl or cycloalkyl, and heterocycloalkyl. Examples include, but are not limited to, formyl, acetyl, ethylcarbonyl, and the like. An aryl group may be substituted or unsubstituted.

As used herein, "alkylamino" means a radical —NHR or —NR2 where each R is, independently, an alkyl group. Examples include, but are not limited to, methylamino, (1-methylethyl)amino, dimethyl amino, methylethylamino, di(1-methylethyl)amino, and the like. An alkylamino may be substituted or unsubstituted.

As used herein, "hydroxyalkyl" means an alkyl radical substituted with one or more hydroxy groups. Representative examples include, but are not limited to, hydroxymethyl, 2-hydroxyethyl; 2-hydroxypropyl; 3-hydroxypropyl; 1-(hydroxymethyl)-2-methylpropyl; 2-hydroxybutyl; 3-hydroxybutyl; 4-hydroxybutyl; 2,3-dihydroxypropyl; 2-hydroxy-1-hydroxymethylethyl; 2,3-dihydroxybutyl; 3,4-dihydroxybutyl and 2-(hydroxymethyl)-3-hydroxy-propyl; preferably 2-hydroxyethyl; 2,3-dihydroxypropyl and 1-(hydroxymethyl)-2-hydroxyethyl. A hydroxyalkyl may be substituted or unsubstituted.

As used herein, "alkenyl" refers to a straight or branched hydrocarbon chain containing one or more double bonds. The alkenyl group may have 2 to 9 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from ethenyl; propen-1-yl; propen-2-yl; propen-3-yl; buten-1-yl; buten-2-yl; buten-3-yl; buten-4-yl; 1-methyl-propen-1-yl; 2-methyl-propen-1-yl; 1-ethyl-ethen-1-yl; 2-methyl-propen-3-yl; buta-1,3-dienyl; buta-1,2,-dienyl and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain comprising one or more triple bonds. The alkynyl group may have 2 to 9 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, e.g., the alkynyl chain is selected from ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "cycloalkyl" means a fully saturated carbocyclyl ring or ring system. Examples include, but are not limited to, cyclopropyl, cyclobutyl, cyclopentyl, and cyclohexyl.

As used herein, "aryl" refers to a carbocyclic (all carbon) monocyclic or multicyclic aromatic ring system (including fused ring systems where two carbocyclic rings share a chemical bond). The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, phenyl, benzyl, α-naphthyl, β-naphthyl, biphenyl, anthryl, tetrahydronaphthyl, fluorenyl, indanyl, biphenylenyl, and acenaphthenyl. Preferred aryl groups are phenyl and naphthyl.

As used herein, "heteroaryl" refers to an aromatic ring or ring system (i.e., two or more fused rings that share two adjacent atoms) that comprise(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, "haloalkyl" refers to an alkyl group, in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl, and 2-fluoroisobutyl. A haloalkyl may be substituted or unsubstituted.

As used herein, a "substituted" group may be substituted with one or more group(s) individually and independently selected from alkyl, alkenyl, alkynyl, cycloalkyl, cycloalkenyl, cycloalkynyl, benzyl, substituted benzyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiol, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group, a di-substituted amino group, and protected derivatives thereof.

As used herein, "halogen" refers to an atom of fluorine, chlorine, bromine or iodine.

As used herein, "homocyclic ring" refers to cycloalkyl or aryl.

As used herein, "heterocyclic ring" refers to a ring, which may contain 1 to 4 hetero-atoms selected from among nitrogen, oxygen, sulfur and other atoms in addition to carbon atoms.

Exemplary cathinones or synthetic cathinones include, but are not limited to, 3, 4-methylenedioxypyrovalerone (MDPV); 4'-methyl-α-pyrrolidinohexanophenone (MPHP); naphyrone; methylone; ethylone; butylone; pentylone; mephedrone; mexedrone; buphedrone; pentedrone; hexedrone; heptedrone; α-pyrrolidinopropiophenone (α-PPP); 4'-methyl-α-pyrrolidinopropiophenone (M-α-PPP); 3',4'-methylenedioxy-a-pyrrolidinopropiophenone (MDPPP); 1-phenyl-2-(1-pyrrolidinyl)-1-pentanone (α-PVP); α-pyrrolidinohexiophenone (α-PHP); α-pyrrolidinoheptiophenone (α-PHpP, PV8); diethylpropion; pyrovalerone; dimethylcathinone; diethylcathinone; methcathinone; ethcathinone; 3-methylmethcathinone (3-MMC); 4-methylethcathinone (4-MEC); 3-chloromethcathinone (3-CMC); 4-chloromethcathinone (4-CMC); n-ethyl-nor-pentedrone (NEP); 3,4-methylenedioxy-a-pyrrolidinobutiophenone (MDPBP); 4-methyl-α-pyrrolidinobutiophenone (MEPBP); 4-fluoromethcathinone (4-FMC); n-ethyl-nor-hexedrone (Hexen); n-ethyl-nor-heptedrone; 4-ethylpentedrone; 4-methyl-NEP; and n-ethyl-nor-pentylone.

In a specific embodiment, the synthetic cathinone is MDPV, mephedrone, ethylone, naphyrone, penthylone, methylone, buthylone, MPHP, 4-MMC, methedrone, pyrovalenrone, MDPBP, α-PVP, MEPBP, 4-FMC, and methcathinone.

Method of Identifying Cross-Reactive Aptamers

The subject invention provides a method of using a novel strategy to isolate and identify nucleic acid aptamers that cross-react with a family of small molecules. The family of small molecules shares a core structure. The aptamers identified and isolated by said method bind to these structurally-similar compounds.

In one embodiment, the method employs a parallel-and-serial SELEX strategy, comprising at least one step of a parallel selection and at least one step of a serial selection. In another embodiment, the method for isolating an aptamer for a family of structurally-similar small molecules comprises: providing a nucleic acid library, mixing the small molecules in said family with the nucleic acid library, binding the small molecules to one or more aptamers in the nucleic acid library, separating the aptamer bound to the small molecules in said family from at least a portion of the unbound nucleic acid molecules, and isolating the aptamer and optionally, amplifying the isolated aptamer.

In one embodiment, the method for isolating a cross-reactive aptamer comprises the steps of:
  providing a nucleic acid library;
  selecting two or more targets from a target family having a core structure to be recognized by the aptamer;
  performing at least one round of a parallel selection against the selected two or more targets in the target family;
  collecting pools of aptamers for each of the selected two or more targets;
  performing at least one cycle of a serial selection against the selected targets in the target family in a sequential order; and
  collecting the cross-reactive aptamer that binds to the selected two or more targets of the target family.

In one embodiment, the target family comprises as many targets as needed that have variations at all desired substituent sites while having the same core molecular framework. The target selection defines the core structure to be recognized by the isolated aptamer, and creates selection pressure for isolating aptamers that are insensitive to the identity of peripheral substituents.

In one embodiment, the target family is synthetic cathinones, a family of designer drugs that share the same beta-keto phenethylamine core structure.

In one embodiment, the nucleic acid library is a DNA library.

As used herein, the terms "nucleic acid library," "polynucleotide library," or the like, generally refer to a mixture of nucleic acid molecules having variable sequence from which an aptamer is selected for a specific target family of small molecules. The oligonucleotides molecules of the library have a length ranging from about 5 to about 500 bases, or to about 450 bases, or to about 400 bases, or to about 350 bases, or to about 300 bases, or to about 250 bases, or to about 200 bases, or to about 150 bases, or to about 100 bases, or to about 50 bases. In some embodiments, the oligonucleotides molecules of the library have a length between about 10 bases and about 100 bases, or between about 20 bases and about 90 bases, or between about 30 bases and about 70 bases, or between about 40 bases and about 60 bases. In certain embodiments, the oligonucleotides molecules of the library have a length of 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 bases.

The constituent molecules of a nucleic acid library may be naturally occurring nucleic acids or fragments thereof (e.g., in a cDNA or EST library), chemically synthesized nucleic acids, enzymatically synthesized nucleic acids or nucleic acids made using any combination of the aforementioned techniques. In some embodiments, each nucleic acid molecule in the library may include one or more fixed (e.g., known) nucleotide sequences 5° to, 3° to, or flanking, the variable region for the purpose of facilitating the enrichment and identification of target aptamers (such as by using PCR, affinity chromatography, or any similar methods used to purify or enrich target nucleic acids).

In one embodiment, the library pool is challenged with at least two, at least three, at least four, at least five, or at least six different targets sharing the same core structure in each parallel selection round, respectively, and then sequentially in a serial selection cycle to isolate an aptamer that can cross-react to at least two, at least three, at least four, at least five, or at least six different targets, and ideally all target-analogs sharing the same core structure. Advantageously, challenging the library pool with more targets from the small-molecule family results in aptamers with broader target-binding spectra and higher cross-reactivity.

In the step of parallel selection, multiple aptamer pools are enriched using each individual target from the target family. Cross-reactive aptamers recognizing the shared core structure are enriched in each of these pools, while aptamers specific to an individual target from the target family are only enriched in their respective pool. Therefore, when all pools are combined after a few rounds of parallel selection, cross-reactive aptamers are highly enriched. The combined pool is then subjected to serial selection with each target molecule sequentially, a process that ultimately retains only those aptamers that bind to the core structure shared by these targets.

In one embodiment, the method uses SELEX strategy for isolating a cross-reactive aptamer for synthetic cathinones, said method comprises the steps of:
  providing a DNA library;
  selecting at least three synthetic cathinone targets;
  performing at least one round of a parallel selection against each selected synthetic cathinone target to isolate a pool of aptamers for each selected synthetic cathinone target;
  collecting the isolated pools of aptamers for each selected synthetic cathinone target;
  combining the isolated pools of aptamers for each selected synthetic cathinone target;
  performing at least one cycle of a serial selection against each selected synthetic cathinone target in each round sequentially; and
  collecting the cross-reactive aptamer.

In one embodiment, the DNA library comprises more than one library pools. The same or different library pools may be used for each of the synthetic cathinones in the family. In a specific embodiment, the DNA library comprises $6 \times 10^{14}$ oligonucleotides. Each library strand is stem-loop structured and has 73 nucleotides in length, with an 8-base-pair stem and a randomized 30 nucleotide loop.

In a preferred embodiment, the DNA library comprises a sequence of SEQ ID NO: 1 where N represents a random base and N30 represents the randomized 30 nucleotides. The randomized nucleotides are each independently selected from adenine (A), thymine (T), cytosine (C), and guanine (G). Preferably, the randomized region has a sequence selected from SEQ ID NOs: 7-17.

In one embodiment, the cross-reactive aptamer isolated by the method according to the subject invention is capable of binding to synthetic cathinones that share the same core structure.

In a further embodiment, the synthetic cathinone family includes, but not limited to, α-PVP, ethylone, butylone, pyrovalerone, MPHP, 4-MMC, MDPV, methedrone, naphryone, MDPBP, 3-FMC, 4-FMC, pentylone, methcathinone, methylone, and MEPBP.

In a specific embodiment, the method uses three targets, α-PVP, ethylone, and butylone from the target synthetic cathinone family for both parallel selection and serial selection. Parallel selection is performed using three different initial library pools, with one pool being challenged with each of α-PVP, ethylone and butylone. In some embodiments, the parallel selection is performed for at least 2, 3, 4, 5, 6, 7, 8, 9, 10, 11, 12, 13, 14, 15, 16, 17, 18, 19, or 20 rounds. In each round, the targets may be used at same or different concentrations. Preferably, the targets may be used in a round of the parallel selection at a lower concentration than that used in the previous round because reducing target concentration round-by-round increases selection stringency.

In one embodiment, the method further comprises performing counter-SELEX against at least one structurally-similar non-cathinone molecule in each round of the parallel selection, preferably, prior to the positive selection. The structurally-similar non-cathinone molecules include, but are not limited to, acetaminophen, amphetamine, cocaine, ephedrine, lidocaine, methamphetamine, procaine, promazine, and pseudoephedrine. Counter-SELEX against structurally-similar non-cathinone molecules eliminates the non-specific binding aptamers and ensures that the selected and enriched aptamer has high specificity to synthetic cathinones. In some embodiments, the number of counter targets and the concentrations of counter targets are progressively increased during the selection process to increase selection stringency.

In specific embodiments, the parallel selection is performed for five rounds. During the first round of the parallel selection, each initial library pool is challenged with a high concentration of targets (e.g., 1000 μM), and eluted strands are collected and amplified by PCR for the next round of selection. In the beginning of the second round, counter-SELEX is performed against structurally-similar non-cathinone molecules. In round two, counter-SELEX is first performed for each pool against cocaine (e.g., 100 μM) with positive selection then performed with a lower concentration of target (e.g., 500 μM). In the third round, the same target concentration is used but an additional counter-target (e.g., 100 μM procaine) is included. In rounds four and five, counter-SELEX is performed against cocaine, procaine, and lidocaine each at a concentration of, for example, 100 μM in a mixture with a further lowered concentration of target (e.g., 250 μM) for positive selection. After the fifth round, a gel elution assay is utilized to determine the target-binding affinity of each pool to their respective target.

In one embodiment, the serial selection is performed to enrich cross-reactive aptamers and exclude aptamers only specific to individual target. The serial selection may be performed more than one cycle, in which the aptamer library is selected against each target of the compound family in a sequential order. Specifically, the serial selection comprises the steps of:

provriding an aptamer library that is obtained by combining each pool obtained from the parallel selection, challenging the aptamer library with targets of the synthetic cathinone family sequentially for at least one cycle with one target being used in each round within one cycle, and collecting a pool of aptamers, the pool consisting of cross-reactive aptamers binding to synthetic cathinones that share the same core structure.

In one embodiment, the serial selection further comprises performing counter-SELEX against at least one structurally-similar non-cathinone molecule in each round of the challenge prior to the positive selection against the target molecule in each cycle of the serial selection. The structurally-similar non-cathinone molecules include, but are not limited to, acetaminophen, amphetamine, cocaine, ephedrine, lidocaine, methamphetamine, procaine, promazine, and pseudoephedrine.

In one embodiment, the method for isolating a cross-reactive aptamer for synthetic cathinones comprises the steps of:

providing a aptamer library, the library being SEQ ID NO: 1;

performing at least one round of parallel selection against α-PVP, ethylone, and butylone, respectively;

collecting three pools of aptamers, each pool being specific to α-PVP, ethylone, or butylone;

obtaining a combined pool of aptamer by combining the aptamer pools each specific to α-PVP, ethylone, and butylone;

performing at least one cycle of serial selection against α-PVP, ethylone, and butylone in each round in a sequential order; and collecting the cross-reactive aptamer for synthetic cathinones.

In a specific embodiment, the serial selection comprises i) challenging the combined pool against butylone; ii) collecting a first pool of aptamer that binds to butylone; iii) challenging the first pool of aptamer of step ii) against ethylone; iv) collecting a second pool of aptamer, the second pool of aptamer being able to bind to both butylone and ethylone; v) challenging the second pool of aptamer of step iv) against α-PVP; and vi) collecting a third pool of aptamer, the third pool of aptamer being able to bind to all three targets: butylone, ethylone and α-PVP. Advantageously, the third pool of aptamer is the cross-reactive aptamer that binds to other synthetic cathinones having the same core structure as butylone, ethylone and α-PVP.

In one embodiment, the method further comprises evaluating the cross-reactivity and specificity of the resulting pool after each round, each cycle, and each selection using, for example, gel elution assay. The pool affinity towards each target of the tested family increases in each round and/or cycle of the serial selection.

In some embodiments, the method further comprises amplifying the resulting pool of aptamers through PCR prior to the next round/cycle/selection. The method further comprises purifying the cross-reactive aptamer from the final enriched pool and amplifying the purified cross-reactive aptamer.

Importantly, the parallel-and-serial selection strategy is designed to promote the enrichment of aptamers that identify the core structure shared by a given target family while being tolerant to side-chain substituents. Rational target selection defines the targeted core structure, and the use of parallel and serial selection forces the isolation of desired cross-reactive aptamers. The strategy described herein can be used to isolate cross-reactive aptamers for other families and classes of structurally-related small molecules in applications such as medical diagnostics, environmental monitoring, food safety, and forensic science.

Cross-Reactive Aptamers

In one embodiment, the cross-reactive aptamers are identified using the parallel-and-serial selection strategy according to the subject invention. The cross-reactive aptamers are capable of binding to a core structure of structurally-similar compounds in a family of interest.

In one embodiment, the cross-reactive aptamer is an oligonucleotide, such as DNA or RNA molecules and may be single-stranded or double-stranded. In a preferred embodiment, the aptamer is a DNA aptamer.

The cross-reactive aptamer may be partially or fully folded to form various secondary structures (e.g., stems, loops, bulges, pseudoknots, G-quadruplexes and kissing hairpins), which in turn can form unique three-dimensional architectures able to specifically recognize their targets by exploiting a variety of interactions—such as hydrophobic and electrostatic interactions, hydrogen bonding, van der Waals forces, and π-π stacking as well as shape complementarity.

As used herein, the terms "polynucleotide," "nucleotide," "oligonucleotide," and "nucleic acid" refer to a nucleic acid comprising DNA, RNA, derivatives thereof, or combinations thereof.

In certain embodiments, the cross-reactive aptamer according to the present invention may comprise at least 20, at least 30, at least 40, at least 50, at least 60, at least 70, or at least 80 nucleotides. The cross-reactive aptamer, preferably, comprises 20 to 200 nucleotides, preferably 25 to 150 nucleotides, more preferably 30 to 100 nucleotides, most preferably, 35 to 60 nucleotides.

In certain embodiments, the cross-reactive aptamer according to the present invention has a minimum length of, for example, 20, 21, 22, 23, 24, 25, 26, 27, 28, 29, 30, 31, 32, 33, 34, 35, 36, 37, 38, 39, or 40 nucleotides. The aptamer according to the present invention may have a maximum length of, for example, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 nucleotides. The aptamer according to the present invention may have a length of, for example, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 nucleotides.

In some embodiments, the cross-reactive aptamers have free ends. For example, the 3' and 5' ends may not be ligated to form a loop, although they may be conjugated to other molecules or otherwise modified. The aptamers may adopt a tertiary structure such as a hairpin loop.

In certain embodiments, the cross-reactive aptamer comprises at least one stem, two stems, or three stems. Each stem may be fully or partially complementary. Each stem may comprise the same or a different number of nucleotides. Exemplary lengths of each stem may be 2, 3, 4, 5, 6, 7, 8, 9, 10, 11, 12, 13, 14, or 15 base pairs. A partially complementary stem may comprise more than one wobble base pair, including, but not limited to, G-U, and T-G.

In one embodiment, the cross-reactive aptamer comprises at least one junction, which is formed when two or more stems meet. In certain embodiments, the junction may be a loop between two stems, or a three-way junction (TWJ). The junction in an aptamer can serve as a binding domain for a small-molecule target.

In one embodiment, the cross-reactive aptamer has at least one hairpin/stem-loop structure. The loop may have a minimum length of, for example, 4, 5, 6, 7, 8, 9, 10, 11, 12, 13, 14, 15, 16, 17, 18, 19, 20, 21, 22, 23, 24, 25, 26, 27, 28, 29, or 30 nucleotides. The loop may have a maximum length of, for example, 40, 41, 42, 43, 44, 45, 46, 47, 48, 49, 50, 51, 52, 53, 54, 55, 56, 57, 58, 59, or 60 nucleotides. The loop may comprise, for example, 20, 21, 22, 23, 24, 25, 26, 27, 28, 29, 30, 31, 32, 33, 34, 35, 36, 37, 38, 39, or 40 nucleotides. In a specific embodiment, the loop comprises 28 nucleotides. The loop region is the target-binding site of the aptamer.

In a specific embodiment, the cross-reactive aptamer recognizes the core structure of synthetic cathinones and binds to all synthetic cathinones. The synthetic cathinones include, but are not limited to MDPV, ethylone, naphyrone, penthylone, methylone, buthylone, MPHP, 4-MMC, methedrone, pyrovalenrone, MDPBP, α-PVP, MEPBP, 4-FMC, and methcathinone.

In specific embodiments, the cross-reactive aptamers selected using the parallel-and-serial selection strategy are synthetic-cathinone-binding aptamers. In a further embodiment, the cross-reactive aptamer is a DNA aptamer comprising 46 nucleotides. In some embodiments, the cross-reactive aptamer comprises a stem and a loop region, the loop region having a sequence selected from SEQ ID NOs: 7-17.

In a preferred embodiment, the cross-reactive aptamer is SCA2.1 (SEQ ID NO: 6) or sequences sharing at least 50%, 55%, 60%, 65%, 70%, 75%, 80%, 85%, 90%, 95% or 99% identity with SCA2.1 (SEQ ID NO: 6). SCA2.1 may be folded as a stem-loop structure or may comprise two hairpin structures. The structure of SCA2.1 may vary when it is present in buffers with different salt concentrations. In a specific embodiment, SCA2.1 comprises a 9-base-pair stem and a 28-nucleotide loop.

SCA2.1 recognizes the beta-keto phenethylamine core structure of synthetic cathinones and binds to synthetic cathinones. Variations in the side chains do not significantly affect target-binding affinity. SCA2.1 does not cross-react with interferents such as pseudoephedrine, promazine, procaine, ephedrine, acetaminophen, methamphetamine, lidocaine, amphetamine, cocaine, sucrose, and caffeine.

The cross-reactive aptamer of the present invention may be chemical modified. The chemical modifications as described herein include a chemical substitution at a sugar position, a phosphate position, and/or a base position of the nucleic acid including, for example, incorporation of a modified nucleotide, incorporation of a capping moiety (e.g., 3' capping), conjugation to a high molecular weight, non-immunogenic compound (e.g., polyethylene glycol (PEG)), conjugation to a lipophilic compound, and substitutions in the phosphate backbone. Base modifications may include 5-position pyrimidine modifications, modifications at exocyclic amines, substitution of 4-thiouridine, substitution of 5-bromo- or 5-iodo-uracil, and backbone modifications. Sugar modifications may include 2'-amine nucleotides (2'-NH2). 2'-fluoronucleotides (2'-F), and 2'-O-methyl (2'-OMe) nucleotides. Such modifications may improve the stability of the aptamers or make the aptamers more resistant to degradation. In some embodiments, each base of a given type (e.g., A, T, C, and G) may contain the same chemical modification.

The cross-reactive aptamers may be modified by addition of one or more reporter labels (or detectable labels). In some embodiments, the label may be attached to either the 5' or 3' end of the aptamer. The label may also be attached to the backbone of the aptamer. The skilled person will be aware of techniques for attaching labels to nucleic acid strands. The detectable label may be attached directly or indirectly to the nucleic acid aptamer. If the label is indirectly attached to the nucleic acid aptamer, it may be by any mechanism known to one of skill in the art, such as using biotin and streptavidin.

The cross-reactive aptamers may comprise a reporter label, such as a fluorescent dye, nanoparticle, or an enzyme. Exemplary labels include, but are not limited to, an organic donor fluorophore or an organic acceptor fluorophore, a luminescent lanthanide, a fluorescent or luminescent nanoparticle, an affinity tag such as biotin, or a polypeptide. In some embodiments, the aptamer may comprise a fluorescent label, for example, fluorescein, TAMRA, rhodamine, Texas Red, Alexa Fluor (e.g., AlexaFluor 488, AlexaFluor 532, AlexaFluor 546, AlexaFluor 594, AlexaFluor 633 and AlexaFluor 647), cyanine dye (e.g., diethylthiatricarbocyanine (Cy7), Cy7.5, Cy5, Cy5.5 and Cy3), Tye dye (e.g., TYE 563, TYE 665, TYE 705), atto dye (e.g., Atto 594 and Atto 633), Hexachlorofluorescein, FAM (6-carboxyfluroescein), BODIPY FL, OliGreen, 40,6-diamidino-2-phenylindol (DAPI), Hoechst 33,258, malachite green (MG), and FITC. The nanoparticle can be an upconversion nanoparticle. In some embodiments, the fluorophore is selected from the group consisting of fluorophores that emit a blue, green, near red or far red fluorescence.

In one embodiment, the reporter label is a fluorescent dye and quencher pair. The quenchers can be, for example, Dabcyl, DDQ-I, Eclipse, Iowa Black FQ, BHQ-1, QSY-7, BHQ-2, DDQ-II, Iowa Black RQ, QSY-21, or BHQ-3.

In one embodiment, the reporter label can be an electroactive molecule, for example, methylene blue, ferrocene, or all enzymes that can convert nonelectroactive substrates into electroactive products.

In one embodiment, the cross-reactive aptamer can bind to a dye such as a fluorophore within the target binding domain or the loop domain. In a preferred embodiment, the dye is diethylthiatricarbocyanine (Cy7).

In one embodiment, the cross-reactive aptamer has inherent dye-displacement functionality. A dye can bind within the target binding domain or the loop domain of the cross-reactive aptamer, and can be displaced in the presence of a small-molecule target, resulting in a change in absorbance, color, or fluorescence. Such change may occur within seconds. Such change can also directly reflect the extent of target binding and be used for detection and quantitative measurement of the target concentration.

In one embodiment, the cross-reactive aptamer binds to the small-molecule target with a dissociation constant of, for example, about 1 µM, about 2 µM, about 3 µM, about 4 µM, about 5 µM, about 6 µM, about 7 µM, about 8 µM, about 9 µM, or about 10 µM. In specific examples, the aptamer binds to the small molecule with a dissociation constant between about 0.001 µM and about 1000 µM, between about 0.01 µM and about 500 µM, between about 0.1 µM and about 200 µM, between about 0.5 µM and about 100 µM, between about 1 µM and about 100 µM, between about 1 µM and about 50 µM, between about 1 µM and about 30 µM, between about 1 µM and 20 µM, or between about 1 µM and about 10 µM.

Method of Using the Cross-Reactive Aptamer

The subject invention provides aptamer-based sensors for rapid and naked-eye detection of small-molecule targets. The aptamer-based sensor comprises a cross-reactive aptamer that binds to a core structure of structurally-similar compounds in a family of interest. The subject invention also provides methods of using the aptamer-based sensor for detecting a family of small-molecule targets in a complex sample.

In one embodiment, the subject invention provides an assay employing dye-displacement strategies for the detection of small-molecule targets. In such assay, a small-molecule dye is initially associated with the binding domain of an aptamer. The presence of the small-molecule targets causes displacement of the dye from the binding domain, resulting in an absorbance, color, or fluorescence change.

In one embodiment, the aptamer according to the subject invention does not require any additional labeling or chemical modification. The methods for detecting small molecule targets using such aptamer without any labeling are label-free.

In one embodiment, the subject invention provides a method for rapid and sensitive detection of a family of small-molecule targets in a sample comprising contacting the sample with a aptamer-based sensor selective for the family of small-molecule targets, wherein the aptamer-based sensor comprises a cross-reactive aptamer that binds to the core structure of the family of small-molecule targets and a dye, and detecting the small-molecule target in the sample, wherein the detection of the small-molecule target comprises measuring a signal generated upon binding of the small-molecule targets to the loop domain of the aptamer.

In a specific embodiment, the dye is Cy7. Cy7 is a small-molecule dye that exists in equilibrium between monomer and dimer forms, which has absorbance peaks at 760 and 670 nm, respectively. Cy7 monomer can bind into hydrophobic target-binding domains of aptamers, which results in a significant enhancement of absorbance at 760 nm. The binding of target to the aptamer can displace Cy7 monomer from the binding domain within seconds, which causes the dye to dimerize in aqueous solution. This results in the reduction of absorbance at 760 nm and enhancement of absorbance at 670 nm, which enables Cy7 to be used as a colorimetric indicator for small molecule detection. Also, the signal change may be indicated using the absorbance ratio at 670/760 nm.

In another embodiment, the method further comprises determining the concentration of the small-molecule target in the sample. The determination can comprise comparing the signal generated upon target binding with a standard curve of such signal. For example, the determination based on Cy7 displacement assay comprises comparing the absorbance signal generated upon binding of aptamer-target complex with a standard curve of the absorbance of Cy7, or a standard curve of the absorbance ratio at 670/760 nm. The absorbance read-out can be quantified in seconds by, for example, a microplate-reader or portable photometer, allowing for high-throughput or on-site detection, respectively.

In one embodiment, the cross-reactive aptamer is a synthetic-cathinone-binding aptamer that specifically binds to the synthetic cathinones having the same beta-keto phenethylamine core structure. Preferably, the synthetic-cathinone-binding aptamer has a sequence of SEQ ID NO: 6.

In one embodiment, the synthetic-cathinone-binding aptamer also binds to Cy7 in its target-binding site in the loop region. Thus, the synthetic-cathinone-binding aptamer can be used in Cy7 displacement assay for detecting one or more synthetic cathinones in a sample. With increased concentration of aptamer, a gradual absorbance peak shift from 760 to 775 nm occurs, which shows that absorbance of the monomer can change in different microenvironments, such as when the dye binds to the aptamer. Specifically, Cy7 has a $K_D$ of 1.6 µM at 775 nm. In some embodiment, the signal change may be indicated using the absorbance ratio at 670/775 nm.

In one embodiment, the method for rapid, sensitive and naked-eye detection of synthetic cathinones in a sample comprises contacting the sample with a aptamer-based sensor selective for synthetic cathinones, wherein the aptamer-based sensor comprises a cross-reactive aptamer that binds to synthetic cathinones and Cy7, and detecting whether a change in color occurs, the change in color being indicative of the presence of the synthetic cathinones in the sample.

In such assay, Cy7 is initially associated with the binding domain of the synthetic-cathinone-binding aptamer. The presence of synthetic cathinones causes the displacement of Cy7 from the binding domain, resulting in a reduction of absorbance at 775 nm and enhancement of absorbance at 670 nm, resulting in a color change from colorless to bright blue that can be detected by naked eyes.

In some embodiments, the dye, e.g., Cy7 may be used at a concentration ranging from about 1 µM to about 50 µM, from about 1 µM to about 40 µM, from about 1 µM to about 30 µM, from about 1 µM to about 20 µM, from about 1 µM to about 10 µM, from about 1 µM to about 9 µM, from about 1 µM to about 8 µM, from about 1 µM to about 7 µM, from about 1 µM to about 6 µM, from about 2 µM to about 6 µM, about 2.2 µM to about 6 µM, about 2.5 µM to about 6 µM, about 3 µM to about 6 µM, and from about 3.5 µM to about 5 µM. In certain embodiments, the dye, e.g., Cy7 is used at a concentration of 2.5 µM, 2.8 µM, 3 µM, 3.2 µM, 3.3 µM, 3.4 µM, 3.5 µM, 3.6 µM, 3.7 µM, 3.8 µM, 3.9 µM, 4 µM, 4.2 µM, 4.5 µM, 4.8 µM or 5 µM. In a preferred embodiment, Cy7 is used at a concentration of 3.5 µM.

Advantageously, the assay has excellent specificity because the aptamer does not cross-react to non-synthetic cathinone interferents. Also, the colorimetric Cy7-displacement assay can detect nanomolar synthetic cathinone concentrations, even in urine and saliva in a label-free manner via instrumental means. This colorimetric Cy7-displacement assay can also achieve instantaneous detection of as low as 6.3 µM target (e.g., ethylone) with the naked-eye when Cy7 is used at a micromolar concentration.

The method of the subject invention is remarkably simple, fast and specific. For example, the detection can be performed in a single tube containing the aptamer-based sensor and the sample of interest. Notably, this method is more cross-reactive to synthetic cathinones than any existing immunoassays while being more cost-effective (30 cent/sample) and having a detection limit suitable for screening of these drugs in biosamples.

The methods of the subject invention can be label-free and, in certain embodiments, can detect synthetic cathinones with the naked eye within seconds. Because the color intensity of the solution is proportional to the concentration of synthetic cathinones, the method of the subject invention can be used to determine the concentration of synthetic cathinones in the sample.

In one embodiment, the method according to the subject invention allows for the visual detection of a variety of synthetic cathinones including, but are not limited to, α-PVP, ethylone, buthylone, naphyrone, MDPV, pentylone, methylone, 4-MMC, 4-FMC, cathinone, 3-FMC, and methcathinone.

In one embodiment, the subject invention provides a method for generating cross-reactive aptamers with structure-switching functionality and a means of rapid and sensitive detection of a small-molecule target family. The generation of a structure-switching cross-reactive aptamer entails digesting the cross-reactive aptamer with an exonuclease mixture, such as Exo III and Exo I.

In one embodiment, the cross-reactive aptamer is truncated from the 3' and/or 5' end by nucleases, such as Exo III and Exo I that exhibit 3'-to-5' exonuclease activity on double-stranded and single-stranded DNA, respectively. Exo III is sensitive to local structural changes in double-stranded DNA induced by small-molecule binding. Exo III catalyzes 3'-to-5' digestion of aptamers by a stepwise removal of mononucleotides, forming single-stranded products. Exo I specifically digests single-stranded nontarget-bound unfolded aptamers, but is resistant to target-bound folded aptamers. A combined Exo III and Exo I digestion generates truncated aptamers with structure-switching functionality. In certain embodiments, such truncation or digestion of an aptamer may be stopped at least 1, 2, 3, 4, 5, 6, 7, 8, 9, 10, 11, or 12 nucleotides or base pairs prior to the target-binding site. Such truncated or digested aptamer product is at least 1, 2, 3, 4, 5, 6, 7, 8, 9, 10, 11, or 12 nucleotides or base pairs shorter compared to the pre-folded aptamer before the truncation or digestion by the exonuclease mixture.

The resulting digestion product has structure-switching functionality with similar or equal affinity as its parent cross-reactive aptamer. In the absence of the target, the truncated aptamer exists in an unfolded single-stranded state while in the presence of the target, the truncated aptamer folds into a double-strand structure with the target binding in the binding domain. Such structure-switching cross-reactive aptamer can be directly employed in folding-based aptamer sensors.

In specific embodiments, the truncated or digested aptamer has a stem comprising a sticky end or a blunt end. The truncated aptamer having a sticky end comprises a 5' or 3' overhang. 5'-3'-tandem-truncated aptamer has a stem comprising a blunt end.

In a specific embodiment, the structure-switching cross-reactive aptamer is SCA-SW-40 (SEQ ID NO: 18), SCA-SW-34 (SEQ ID NO: 19) or sequences sharing at least 50%, 55%, 60%, 65%, 70%, 75%, 80%, 85%, 90%, 95% or 99% identity with SCA-SW-40 (SEQ ID NO: 18) or SCA-SW-34 (SEQ ID NO: 19). SCA-SW-40 (SEQ ID NO: 18) comprises nucleotides 1-40 of SEQ ID NO: 6 while SCA-SW-34 (SEQ ID NO: 19) comprises nucleotides 7-40 of SEQ ID NO: 6.

In one embodiment, the subject invention provides a method for detecting a small molecule target or a small-molecule target family in a sample using the structure-switching cross-reactive aptamer.

In one embodiment, the subject invention provides methods for rapid and sensitive detection of a small-molecule target or a small-molecule target family in a sample by incorporating the structure-switching cross-reactive aptamers into an electrochemical aptamer-based (E-AB) sensor, which has demonstrated target-induced conformational changes within the aptamers and has achieved excellent sensor performance. The method comprises contacting the sample with the E-AB sensor, and detecting the small-molecule target/target family in the sample, wherein the detection of the small-molecule target comprises measuring a signal generated from a signal reporter.

In one embodiment, the E-AB sensor comprises a structure-switching cross-reactive aptamer, and an electrode, wherein the structure-switching cross-reactive aptamer is labeled with a redox tag at one end and a functional group at the other end, and wherein the structure-switching cross-reactive aptamer is conjugated to the surface of the electrode via the functional group. The functional groups include, but are not limited to, thiol, sulfide, disulfide, amide, ester, alkenyl, alkynyl, carbonyl, aldehyde, carboxylate, carboxyl, and carbonate ester groups. Preferably, the functional group is thiol, and the redox tag is a methylene blue (MB) redox tag, which may label the aptamer at the 5' end, and 3' end via a linker having 1-10 carbons, preferably, a linker having 6 or 7 carbons.

In the absence of a target, the structure-switching cross-reactive aptamer is primarily unfolded, prohibiting electron transfer from the redox tag to the electrode. In the presence of a target, the structure-switching cross-reactive aptamer undergoes a target-induced conformational change that brings the redox tag close to the electrode surface, facilitating efficient electron transfer and resulting in an increase in current within seconds. In a further embodiment, the detection of the small-molecule target comprises measuring a signal generated upon binding of the small-molecule target with the E-AB sensor, wherein the signal is an increase in current.

In one embodiment, the electrode is made of, for example, gold, silver, or platinum. The electrode may have any shape suitable for the E-AB sensor. Exemplary shapes of electrode include, but are not limited to, rod, sheet, plate, and disc. The electrode may have a size ranging from about 100 nm to about 50 mm, from about 500 nm to about 10 mm, from about 1 mm to about 5 mm. In a specific embodiment, the electrode has a diameter about 3 mm.

In certain embodiments, the aptamer is immobilized on the electrode of the E-AB sensor at a density ranging from about $1 \times 10^{10}$ to about $1 \times 10^{15}$, about $5 \times 10^{10}$ to about $5 \times 10^{14}$, about $1 \times 10^{11}$ to about $1 \times 10^{14}$, about $5 \times 10^{11}$ to about $5 \times 10^{13}$, about $1 \times 10^{12}$ to about $5 \times 10^{13}$, and about $1 \times 10^{12}$ to about $1 \times 10^{13}$ molecules/cm$^2$. In specific embodiment, the aptamer is immobilized on the electrode at a density of $0.73 \times 10^{12}$, $1.02 \times 10^{12}$, $1.5 \times 10^{12}$, $1.57 \times 10^{12}$, $3 \times 10^{12}$, $3.2 \times 10^{12}$, $7.3 \times 10^{12}$, or $12 \times 10^{12}$ molecules/cm$^2$.

In one embodiment, the E-AB sensor further comprises a backfiller to fill vacant areas on the electrode surface. The backfiller includes DTT, MCH, and/or a combination thereof. The backfiller is immobilized on the surface of the electrode, for example, via thiol-gold chemistry.

In certain embodiments, the backfiller may be used at concentrations between about 10 µM to about 50 mM, from about 100 µM to about 40 mM, from about 200 µM to about 30 mM, from about 500 µM to about 20 mM, from about 1 mM to about 10 mM, from about 2 mM to about 9 mM, and from about 2 mM to about 5 mM. In a preferred embodiment, the backfiller is used, either alone or in combination, at a concentration of 1 mM, 2 mM, 3 mM, 4 mM, or 5 mM.

In a specific embodiment, the E-AB sensor comprises a structure-switching cross-reactive aptamer, and an electrode, wherein the electrode is a gold electrode, wherein the structure-switching cross-reactive aptamer is labeled with a 5' thiol and a 3' methylene blue (MB) redox tag, and conjugated to a gold electrode surface via thiol-gold chemistry.

In one embodiment, the method further comprises determining the concentration of the small-molecule target in the sample. The determination comprises comparing the current generated upon binding of the small-molecule target with the E-AB sensor with a standard curve. The read-out can be quantified in seconds by, for example, a voltmeter or a potentiostat. Thus, the current measured upon binding of the small-molecule target with the E-AB sensor is indicative of the presence of the small-molecule target in such sample.

In one embodiment, the method according to the subject invention can be used to detect one or more synthetic cathinones in a sample. The method comprises contacting the sample with an E-AB sensor, wherein the E-AB sensor comprises a structure-switching cross-reactive aptamer selective for synthetic cathinones and the structure-switching cross-reactive aptamer is conjugated to the surface of a gold electrode; and detecting one or more synthetic cathinones in the sample, wherein the detection comprises measuring a current generated upon binding of synthetic cathinones with the E-AB sensor. Advantageously, this method using E-AB sensor can detect synthetic cathinones in a sample within 10 seconds of the reaction.

In one embodiment, the E-AB sensor is used to detect synthetic cathinones in a buffer solution comprising at least one salt containing, for example, $Mg^{2+}$ and/or $Na^+$. The salt may be, for example, $MgCl_2$ and/or NaCl. The salt may be used at the physiological concentration or any concentrations suitable for maintaining the function and binding affinity of isolated aptamers and the E-AB sensor.

Exemplary concentrations of magnesium salt may be between about 0 mM and about 50 mM, between about 0.1 mM and about 40 mM, between about 0.2 mM and about 30 mM, between about 0.5 mM and about 20 mM, between about 1 mM and about 15 mM, between about 2 mM and about 10 mM, between about 3 mM and about 8 mM, between about 0 mM and about 5 mM, between about 0 mM and about 2 mM, between about 0 mM and about 1 mM, between about 0.01 mM and about 0.5 mM, and between about 0.02 mM and about 0.1 mM. In a specific embodiment, the concentration of magnesium salt is 0.03 mM or 5 mM.

Exemplary concentrations of sodium salt may be between about 0 mM and about 50 mM, between about 0 mM and about 40 mM, between about 0 mM and about 30 mM, between about 0 mM and about 20 mM, between about 0 mM and about 15 mM, between about 0 mM and about 10 mM, between about 0 mM and about 5 mM, between about 0 mM and about 1 mM, between about 0.05 mM and about 1 mM, and between about 0.1 mM and about 0.5 mM. In a specific embodiment, the concentration of sodium salt is 0 or 0.1 mM.

In a specific embodiment, the structure-switching cross-reactive aptamer (e.g., SCA-SW-40 or SCA-SW-34) is modified with a 5' thiol and a 3' methylene blue redox tag. The thiol group may be linked to the 5' end of the aptamer via a first linker and the methylene blue redox tag may be linked to the 3' end of the aptamer via a second linker. The first and second linkers may be different or identical. Each of the first and second linkers independently comprises 1-10 carbons. Preferably, each of the first and second linkers independently comprises 2-8 carbons. More preferably, the first linker is a 6-carbon linker (i.e., $-(CH_2)_6-$) and the second linker is a 7-carbon linker (i.e., $-(CH_2)_7-$).

In some embodiments, the aptamer according to the subject invention may be used at a concentration ranging from about 1 nM to about 10 mM, about 10 nM to about 5 mM, about 20 nM to about 2 mM, about 50 nM to about 1 mM, about 100 nM to about 500 µM, about 200 nM to about 200 µM, about 500 nM to about 100 µM, about 1 µM to about 50 µM, from about 1 µM to about 40 µM, from about 1 µM to about 30 µM, from about 1 µM to about 20 µM, from about 1 µM to about 10 µM, from about 2 µM to about 9 µM, from about 2 µM to about 8 µM, from about 2 µM to about 7 µM, from about 3 µM to about 6 µM, from about 4 µM to about 6 µM, and from about 5 µM to about 6 µM. In specific embodiments, the aptamer according to the subject invention may be used at a concentration of 1 nM, 10 nM, 20 nM, 25 nM, 50 nM, 100 nM, 200 nM, 500 nM, 1 µM, 2 µM, 3 µM, 4 or 5 µM.

In one embodiment, the method according to the subject invention can achieve superior sensitivity for target detection at low micromolar or nanomolar concentration, for example, as low as about 200 µM, about 150 µM, about 100 µM, about 10 µM, about 1 µM, about 100 nM, about 10 nM, or about 1 nM.

In one embodiment, the methods for small molecule detection provided herein are rapid and can be completed in about 5 minutes to about 120 minutes, about 6 minutes to about 110 minutes, about 7 minutes to about 100 minutes, about 8 minutes to about 90 minutes, about 9 minutes to about 80 minutes, about 10 minutes to about 70 minutes about 15 minutes to about 60 minutes, about 20 minutes to about 50 minutes, or about 25 minutes to about 40 minutes. In some embodiments, the method can be completed in about 5 minutes, about 10 minutes, about 15 minutes, about 20 minutes, about 25 minutes, about 30 minutes, about 35 minutes, about 40 minutes, about 45 minutes, or about 50 minutes.

In another embodiment, the methods for small molecule detection provided herein are rapid and can be completed in about 5 seconds to about 5 minutes, about 10 seconds to about 4 minutes, about 15 seconds to about 3 minutes, about 20 seconds to about 2 minutes, or about 25 seconds to about 1 minute.

In one embodiment, the subject invention provides a method for detecting small molecules that are biomarkers for diagnosis of a disease or condition, or monitoring therapeutic response to specific treatments. In specific embodiments, the condition can be, for example, cancer, an injury, an inflammatory disease or a neurodegenerative disease. In some embodiments, the condition can be substance abuse, psychosis, schizophrenia, Parkinson's disease, attention deficit hyperactivity disorder (ADHD), and pain. In some embodiments, the pain is acute pain or chronic pain. In some embodiments, the pain is neuropathic pain, e.g., chronic neuropathic pain.

In one embodiment, the methods, assays and products according to the subject invention can be used for the sensitive and accurate detection of small-molecule targets in fields including environmental monitoring, food safety, law enforcement, medical diagnostics, and public health.

The subject invention encompasses the use of sequences having a degree of sequence identity with the nucleic acid sequence(s) of the present invention. A similar sequence is taken to include a nucleotide sequence which may be at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the subject sequence. Typically, the similar sequences will comprise the same or similar secondary structure as the subject nucleic acid aptamer. In one embodiment, a similar sequence is taken to include a nucleotide sequence which has one or several additions, deletions and/or substitutions compared with the subject sequence.

The term "about" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%).

EXAMPLES

Experimental Section
Materials and Methods
Materials

The names and sequences of the DNA oligonucleotides (5'-3') are listed below, where N represents random base; /Bio/ represents biotin modification; and MB represents methylene blue. All DNA oligonucleotides were dissolved in PCR quality water. The concentrations of dissolved DNA were measured using a NanoDrop 2000 spectrophotometer.

Library:
(SEQ ID NO: 1)
5'-CGA GCA TAG GCA GAA CTT ACG AC(N30) GTC GTA AGA GCG AGT CAT TC-3' cDNA-bio:
(SEQ ID NO: 2)
5'-TTT TTG TCG TAA GTT CTG CCA TTT T/Bio/-3'

Forward primer (FP):
(SEQ ID NO: 3)
5'-CGA GCA TAG GCA GAA CTT AC-3'

RP-bio:
(SEQ ID NO: 4)
5'-/Bio/GAA TGA CTC GCT CTT ACG AC-3'

Reverse primer (RP):
(SEQ ID NO: 5)
5'-GAA TGA CTC GCT CTT ACG AC-3'

SCA 2.1:
(SEQ ID NO: 6)
5'-CTT ACG ACC TTA AGT GGG GTT CGG GTG GAG TTT ATG GGG TCG TAA G-3'

SCA-SW-40:
(SEQ ID NO: 18)
5'-CTT ACG ACC TTA AGT GGG GTT CGG GTG GAG TTT ATG GGG T-3'

SCA-SW-34:
(SEQ ID NO: 19)
5'-ACC TTA AGT GGG GTT CGG GTG GAG TTT ATG GGG T-3'

Drug standards, including 3,4-methylenedioxypyrovalerone (MDPV), 3-fluoromethcathinone (3-FMC), 4-methylmethcathinone (4-MMC), 4-fluoromethcathinone (4-FMC), alpha-pyrrolidinopentiophenone (α-PVP), butylone, cathinone, ethylone, methcathinone, methylone, naphyrone, pentylone, mephedrone, methedrone, 3,4-methylenedioxy-α-pyrrolidinobutiophenone, 4-methyl-a-pyrrolidinobutiophenone, and 4'-methyl-α-pyrrolidinohexanophenone were purchased from Cayman Chemicals. Acetaminophen, amphetamine, benzocaine, caffeine, cocaine, diethylthiatricarbocyanine (Cy7), ephedrine, lidocaine, methamphetamine, procaine, promazine, pseudoephedrine, 2,2'-azinobis (3-ethylbenzthiazoline)-6-sulfonic acid (ABTS), chlorpromazine HCl, cocaine HCl, diphenhydramine HCl, levamisole HCl, lidocaine HCl, methamphetamine HCl, promazine HCl, scopolamine HCl, and sucrose and all other chemicals were purchased from Sigma-Aldrich unless otherwise noted. TOPO TA cloning kit and the plasmid extraction kit (PureLink® Quick Plasmid Miniprep Kit) were purchased from Invitrogen. Tween 20, 30% hydrogen peroxide ($H_2O_2$) and formamide were purchased from Fisher Scientific. 500 μL micro-gravity columns were purchased from Bio-Rad. Streptavidin-coated agarose resin (capacity: 1-3 mg biotinylated BSA/ml resin), One Shot Chemically Competent *Escherichia coli*, and SYBR Gold were purchased from Thermo Scientific. GoTaq Hot Start Colorless Master Mix was purchased from Promega. 3 KDa 3 kDa cut-off spin filters were purchased from Millipore. All synthetic cathinones were purchased as hydrochloride salts.

SELEX Strategy

The isolation of aptamers was carried out following a library-immobilized SELEX protocol with the parallel-and-serial selection strategy. Detailed information regarding the conditions for each round of selection are listed in Table 1. The whole aptamer isolation process consists of 5 (ethylone and butylone) or 9 (α-PVP) rounds of parallel selection and 2 cycles of serial selection.

TABLE 1

Detailed information regarding the conditions for each round of selection

| | Round # | Pool size (pmole) | Counter-targets | Targets |
|---|---|---|---|---|
| Parallel selection | P1 | 1000 | N/A | Butylone (1000 μM) |
| | | 1000 | | Ethylone (1000 μM) |
| | | 1000 | | α-PVP (1000 μM) |
| | P2 | 358 | COC (100 μM) | Butylone (500 μM) |
| | | 346 | | Ethylone (500 μM) |
| | | 368 | | α-PVP (500 μM) |
| | P3 | 321 | COC & PRO (100 μM each) | Butylone (500 μM) |
| | | 362 | | Ethylone (500 μM) |
| | | 345 | | α-PVP (500 μM) |

TABLE 1-continued

Detailed information regarding the conditions for each round of selection

| | Round # | Pool size (pmole) | Counter-targets | | | Targets |
|---|---|---|---|---|---|---|
| | P4 | 319 | COO, PRC, & LDC (100 μM each) | | | Butylone (250 μM) |
| | | 367 | | | | Ethylone (250 μM) |
| | | 292 | | | | α-PVP (250 μM) |
| | P5 | 300 | COC, PRC, & LDC (100 μM each) | | | Butylone (250 μM) |
| | | 300 | | | | Ethylone (250 μM) |
| | | 300 | | | | α-PVP (250 μM) |
| | P6 | 300 | COC, PRC, & LDC (100 μM each) | | | α-PVP (100 μM) |
| | P7 | 300 | COC, PRO, & LDC (100 μM each) | | | α-PVP (100 μM) |
| | P8 | 300 | COC, PRC, & LDC (100 μM each) | | | α-PVP (100 μM) |
| | P9 | 300 | COC (300 μM) | PRC (300 μM) | LDC (300 μM) | α-PVP (100 μM) |
| Serial | S1 | 300* | COC (500 μM) | PRC (500 μM) | LDC (500 μM) | Butylone (100 μM) |
| selection | S2 | 300 | | | | Ethylone (100 μM) |
| | S3 | 300 | | | | α-PVP (100 μM) |
| | S4 | 300 | EPH, PSE, ACM, | COC, PRC, & LDC | Promazine (500 μM) | Butylone (100 μM) |
| | S5 | 300 | METH, & AMP | (1000 μM each) | | Ethylone (100 μM) |
| | S6 | 300 | (500 μM each) | | | α-PVP (100 μM) |

*Consists of 100 pmole each of pool enriched with butylone (Round P5), ethylone (Round P5) and α-PVP (Round P9).
Acetaminophen (ACM), amphetamine (AMP), cocaine (COC), ephedrine (EPH), lidocaine (LDC), methamphetamine (METH), procaine (PRC), pseudoephedrine (PSE).

Parallel Selection

For parallel selections (Round P1-P5 for ethylone and butylone, Round P1-P9 for a-PVP), three initial pools, each consisting of 1000 pmole DNA library, were used for the three different selection targets (α-PVP, ethylone, butylone). Positive selection was performed with progressively decreasing target concentrations (Round P1: 1000 μM, Round P2-P3: 500 μM, Round P4-P5: 250 μM for α-PVP, ethylone and butylone; Round P6-P9: 100 μM only for α-PVP) to increase selection stringency for enriching strong binders. Counter-selection was also performed for each round prior to positive selection, except the first round, to eliminate non-specific binders. The number of counter targets and the concentrations of counter targets were progressively increased during the counter selection process to increase selection stringency. Specifically, from Round P1-P5 for ethylone and butylone pools and Round P1-P9, 100 μM each of cocaine, procaine, and/or lidocaine as a mixture was used, except for Round P9 for the α-PVP pool which employed 300 μM of each aforementioned counter target employed consecutively.

Serial Selection

Once measurable binding affinity was observed for each pool to their respective target after parallel selection, 100 pmole of each individual pool was combined to generate the initial pool for serial selection. Two cycles of serial selection (Cycle 1: Round S1-S3, Cycle 2: Round S4-S6) were performed to specifically isolate cross-reactive aptamers. For each cycle, positive selection was performed by alternating the selection target (Round S1 & S4: butylone, Round S2 & S5: ethylone, and Round S3 & S6: α-PVP). Target concentration was maintained at 100 μM for each round of serial selection for maximum selection stringency to isolate high affinity aptamers. In the first cycle of serial selection, counter-SELEX was performed by consecutively challenging the pool with a mixture of 500 μM each of cocaine, procaine and lidocaine while in the second cycle of serial selection, counter-SELEX was performed by sequential challenging with a mixture of 500 μM each of ephedrine, pseudoephedrine, acetaminophen, methamphetamine, amphetamine; a mixture of 1000 μM each cocaine, procaine, and lidocaine; and 500 μM promazine. From second round to fourth round in parallel selections, approximately 300 pmole of enriched library pool for each target from the previous round were employed in the subsequence round.

SELEX Procedure

The initial ssDNA library used for SELEX consisted of approximately $6 \times 10^{14}$ oligonucleotides. Each library strand is stem-loop structured and 73 nucleotides in length, with an 8-base-pair stem flanked by two fixed primer regions and a randomized 30 nucleotide loop (library: SEQ ID NO: 1). For the first round of SELEX, 1000 pmole of library was mixed with biotinylated capture strands (cDNA-bio: SEQ ID NO: 2) at a molar ratio of 1:5 in selection buffer (10 mM Tris-HCl, 0.5 mM $MgCl_2$, 20 mM NaCl, pH 7.4), heated at 95° C. for 10 minutes, and cooled at room temperature for over 30 minutes to ensure hybridization between library and capture strands. A micro-gravity column was prepared by adding 250 μL of streptavidin-coated agarose beads followed by washing of the column with 250 μL of selection buffer for three times. A 250 μL solution containing the library pool was then flowed through the micro-gravity column three times in order to conjugate the library to the agarose beads. The column was subsequently washed 10 times with selection buffer. Then, 250 μL of target (α-PVP, ethylone or butylone) dissolved in selection buffer was added to the column, and the eluent was collected. This process was repeated an additional two times, and all eluents were combined together (750 μL total).

The resulting pool was concentrated via centrifugation using a 3 KDa cut-off spin filter. The concentrated pool (100 μL) was then mixed with 1 mL of GoTaq Hot Start Colorless Master Mix with 1 μM forward primer (SEQ ID NO: 3) and 1 μM biotinylated reverse primer (RP-bio: SEQ ID NO: 4) to amplify the pool via PCR. Amplification was performed with the following program: 1 cycle of 95° C. for 2 minutes; 13 cycles of 95° C. for 15 seconds, 58° C. for 30 seconds, and 72° C. for 45 seconds; and 1 cycle of 72° C. for 5 minutes using a BioRad C1000 thermal cycler. Amplification of the enriched pool and the absence of byproducts was confirmed using 3% agarose gel electrophoresis.

To generate single-stranded DNA from the resulting double-stranded PCR products, a fresh micro-gravity column was prepared containing 250 μL streptavidin-coated agarose beads. The amplified pool was then flowed through the column three times to conjugate the pool to the beads. Afterwards, the column was washed six times with 250 μL of separation buffer (10 mM Tris-HCl, 20 mM NaCl, pH 7.4). The column was then capped, and 300 µL of a 0.2 M NaOH solution was added to the column and incubated for 10 minutes to generate single-stranded DNA and then the eluent was collected. An additional 100 µL of 0.2 M NaOH was added to elute residual library strands from the column and this eluent was collected. Both eluents were combined and neutralized with 0.2 M HCl and the pool was concentrated via centrifugation with a 3 KDa cut-off spin filter. The same protocol was performed for subsequent rounds of positive selection.

From the second round, counter-SELEX was performed before the target elution step. Specifically, the library-immobilized column was washed with 250 µL of counter-target(s) in selection buffer to remove non-specific DNA strands. This process was repeated three (Round: P1-P3 and S1-S6) or ten (Round: P4-P5 for ethylone and buthylone, P4-P9 for a-PVP) times. Afterwards, the column was washed 30 times with selection buffer to wash away non-specific binders in preparation for positive selection.

Gel Elution Assay

The enrichment and target affinity, specificity, and cross-reactivity of the pools after Rounds P5, P9, S3, and S6 were evaluated using a modified version of a previously reported gel elution assay. Specifically, 50 pmole of enriched library was incubated with 250 pmole of biotinylated cDNA in 125 µL of selection buffer, heated at 95° C. for 10 minutes, and cooled at room temperature for over 30 minutes to anneal both strands. The cDNA-library complex was then mixed with 125 µL of streptavidin-coated agarose beads in a microcentrifugation tube and washed with 625 µL of selection buffer for five times using an end-over-end rotator for 5 minutes followed by centrifugation and removal of the supernatant. The volume of the library-immobilized bead solution was adjusted to 150 µL with selection buffer and aliquoted into 7 tubes (20 µL per tube). Afterwards, 50 µL of varying concentrations of the target (final concentrations: 0, 10, 50, 100, 250, 500, 1000 µM) was added into each tube. After rotating for 60 minutes on an end-over-end rotator, the beads were settled by centrifugation and 40 µL of the supernatant, which contained the target-eluted strands with a concentration of "$c_s$", was collected and set aside. Meanwhile the leftover solution (30 µL) was mixed with 50 µL of a 95% formamide solution containing 10 mM EDTA and incubated at 90° C. for 10 minutes to completely release all DNA strands from the beads.

The resulting solution contained both leftover target-eluted strands and non-target-eluted strands, the concentration of this solution being termed as "$c_b$". The concentration of the target-eluted aptamer solution ($c_s$) and formamide-treated library solution ($c_b$) were analyzed via 15% denaturing polyacrylamide gel electrophoresis (PAGE) and the concentrations of the strands were determined via standardized concentrations of ladder loaded in the gel. The elution percentage was calculated using the equation $$\theta = \frac{V_1 \times c_s}{V_2 \times c_s + V_3 \times c_b} \times 100\%$$

where $\theta$ is the fraction of target-eluted strands, $V_1$ is the volume of solution before collection of the supernatant ($V_1$=62 µL, the volume occupied by agarose beads was estimated as 8 µL), $V_2$ is the volume of the collected supernatant containing target-eluted strands (40 µL), and $V_3$ is the volume of solution after addition of formamide (80 µL).

The same protocol was used to determine the target-cross-reactivity and specificity of the enriched pool affinity for other synthetic cathinones (3-FMC, 4-MMC, 4-FMC, cathinone, MDPV, methcathinone, methylone, naphyrone, and pentylone) or counter-targets (acetaminophen, amphetamine, cocaine, ephedrine, lidocaine, methamphetamine, procaine, promazine, and pseudoephedrine).

Cloning and Sequencing

Cloning and sequencing of the final enriched pool was performed using a previously reported protocol. Briefly, the enriched sequences from the final pool (Round S6) were amplified by PCR with unlabeled forward and reverse primers (FP: SEQ ID NO: 3 and RP: SEQ ID NO: 5) using the same program as described above in 'SELEX Procedure'.

At the end of the amplification protocol, an additional 30-minute extension step at 72° C. was performed to add an A-tail. The PCR product was cloned into a plasmid vector and transformed into E. coli cells using the TOPO TA cloning kit (Invitrogen) according to the supplier recommendations. The plasmids from 50 randomly picked colonies were extracted using a PureLink Quick Plasmid Miniprep Kit (Invitrogen) and sequenced at the Florida International University DNA Core Facility. The sequences of the plasmid and primers were removed, and the resulting aptamer sequences were aligned with the BioEdit software and the consensus sequence was identified using WebLogo.

Isothermal Titration Calorimetry (ITC)

ITC was perforated using a MicroCal ITC200 instrument (Malvern). All ITC experiments were carried out using the following protocol at 23° C. A solution containing the aptamer (final concentration 20 µM) was prepared in selection buffer (10 mM Tris-HCl, 0.5 mM MgCl$_2$, 20 mM NaCl, pH 7.4) and loaded into the ITC sample cell. Then, 0.35 mM of MDPV or other targets in the same buffer was loaded into the syringe and titrated into the cell with an initial 0.4 µL purge injection followed by 19 successive 2 µL injections. A spacing of 180 seconds was used between each titration. The final molar ratio between the target and aptamer was 3.8:1. The heat generated from each titration was recorded and the binding enthalpy ($\Delta H$), entropy ($\Delta S$), and dissociation constant ($K_D$) were obtained by fitting the resulting titration curve with a single-site binding model using the MicroCal analysis kit integrated into Origin 7 software.

Characterization of Cy7 Binding to the Synthetic-Cathinone-Binding Aptamer (SCA2.1)

8 µL of different concentrations of SCA2.1, 8 µL of 20 µM Cy7 (final concentration 2 µM), and 64 µL of reaction buffer (final concentration 10 mM Tris-HCl, 0.5 mM MgCl$_2$, 20 mM NaCl, 0.01% Tween 20, and 1% DMSO, pH 7.4) were mixed in the wells of a 384-well plate. UV-vis spectra were immediately recorded from 450 nm to 900 nm using a Tecan Infinite M1000 PRO microplate reader at room temperature. The absorbance value at 785 nm ($\lambda$max of Cy7 monomer) was plotted against the concentration of added aptamer. The $K_D$ was estimated by non-linear fitting using the Langmuir equation.

Cy7-Displacement Assay for Colorimetric Detection of Synthetic Cathinones

8 µL of SCA2.1 (final concentration: 3 µM), 8 µL of Cy7 (final concentration 2 µM), 8 µL of varying concentrations of α-PVP, butylone, or ethylone, and 56 µL of reaction buffer (10 mM Tris-HCl, 0.5 mM MgCl$_2$, 20 mM NaCl, 0.01% Tween 20, 1% DMSO, pH 7.4) were mixed in the wells of a 384-well plate. UV-vis spectra were immediately recorded from 450 nm to 900 nm using a Tecan Infinite M1000 PRO microplate reader at room temperature. The absorbance ratio between 670 nm and 785 nm ($A_{670}/A_{785}$) were calculated for each sample and signal gain was calculated by $(R-R_0)/R_0$, where $R_0$ and R represent $A_{670}/A_{785}$ without and with targets, respectively. Using the same protocol, the cross-reactivity and specificity of the assay were tested using other synthetic cathinones (naphyrone, MDPV, pentylone, methylone, 4-MMC, 4-FMC, 3-FMC, methcathinone and cathinone) and interferents (amphetamine, methamphetamine cocaine, pseudoephedrine, ephedrine, procaine, lidocaine, benzocaine, caffeine, acetaminophen, and sucrose) at a concentration of 50 μM. Cross-reactivity was calculated using the signal gain of 50 μM α-PVP as 100%. For visual synthetic cathinone detection, the assay was performed using the same protocol but with optimized concentrations of SCA2.1 (5 μM) and Cy7 (3.5 μM) with 50 μM of the aformetioned synthetic cathinones or interferents. Photographs of the samples were taken using a digital camera immediately after mixing all reaction components.

Fabrication of an Electrochemical Aptamer-Based (E-AB) Sensor for Detection of Synthetic Cathinones The E-AB sensor was fabricated by using polycrystalline gold disk electrodes (3 mm diameter; BAS). The electrodes were polished and cleaned by following a previously published protocol (ref). The clean gold electrode was incubated with different concentrations of 5' thiolated, 3' methylene blue-modified SCA-SW-40 or SCA-SW-34 containing 2 mM tris-(2-carboxyethyl) phosphine hydrochloride in phosphate-buffered saline (PBS) (10 mM phosphate, 1 M NaCl, and 1 mM MgCl$_2$, pH 7.2) for 12 hours. The surface was then rinsed with deionized water and passivated with 3 mM 6-mercaptohexanol in the same PBS buffer for 2 hours. The electrode was incubated in a Tris buffer (10 mM Tris, 1 mM NaCl, and 0.03 mM MgCl$_2$, pH 7.4) for 1 hour prior to the measurements. Sensor performance was evaluated by monitoring the electrode in optimized buffer containing different synthetic cathinones and interferents using square wave voltammetry (CH Instruments).

Example 1—Parallel-and-Serial SELEX Strategy to Identify Cross-Reactive Aptamers A rationally designed 'parallel-and-serial' SELEX strategy was developed to isolate cross-reactive aptamers for structurally-similar compounds. The strategy has three elements that are crucial for its success. First, the targets used for SELEX are highly important, as target selection defines the core structure that is to be recognized by the isolated aptamer and also creates selection pressure for isolating aptamers that are insensitive to the identity of peripheral substituents. Thus, as many targets as needed are chosen that have variations at all desired substituent sites while having the same core molecular framework of the target family. Second, the strategy utilizes 'parallel selection', in which multiple aptamer pools are enriched using each individual target. Cross-reactive aptamers recognizing the shared core structure would be enriched in each of these pools, while aptamers specific to an individual target should only be enriched in their respective pool. Therefore, when all pools are combined after a few rounds of parallel selection, cross-reactive aptamers should be highly enriched, thus increasing the likelihood of successful isolation. Third, the combined pool must then be subjected to 'serial selection' with each target sequentially, a process that ultimately retains only those aptamers that bind to the core structure shared by these targets.

This strategy was used to isolate a cross-reactive aptamer binding to synthetic cathinones, a family of designer drugs that share the same chemical core structure with four substituent sites (FIG. 1A). Synthetic cathinones are highly addictive central nervous system stimulants, and are associated with many severe psychological and physiological health consequences. Assay development for the detection of these drugs lags well behind the emergence of new molecules into the market, with current immunoassays only capable of detecting a few members.

Specifically, parallel selection was first performed to enrich cross-reactive synthetic-cathinone-binding aptamers using three targets: α-PVP, ethylone, and butylone (FIG. 1A). These targets share the same beta-keto phenethylamine core structure but have variation at all substitution sites typical of the synthetic cathinone family. Parallel selection was performed using three different initial library pools, with one pool being challenged with α-PVP, one with ethylone, and one with butylone (FIG. 1B).

During the first round, each initial library pool was challenged with 1000 μM of target, and eluted strands were collected and amplified for the next round of selection. To ensure that the aptamer has high specificity, counter-SELEX was performed from the beginning of the second round against structurally-similar non-cathinone molecules including acetaminophen, amphetamine, cocaine, ephedrine, lidocaine, methamphetamine, procaine, promazine, and pseudoephedrine.

In round two, counter-SELEX was first performed for each pool against 100 μM cocaine, with positive selection then being performed with 500 μM target, as reducing target concentration increases selection stringency. In the third round, the same target concentration was used but an additional counter-target (100 μM procaine) was included. In rounds four and five, counter-SELEX was performed against cocaine, procaine, and lidocaine each at a concentration of 100 μM in a mixture with 250 μM target for positive selection. After the fifth round, a gel elution assay was utilized to determine the target-binding affinity of each pool to their respective target. The fraction of eluted library increased with increasing target concentrations for the ethylone (FIG. 2A) and butylone (FIG. 3A) pools, showing that aptamers binding to these targets had been enriched through parallel selection. Meanwhile, target elution remained low and constant for the α-PVP pool (FIG. 4A) regardless of the employed concentration of target, which indicated that the pool was not yet enriched.

The cross-reactivity and specificity of the three pools were further determined via the gel-elution assay. Both the enriched ethylone and butylone pools were able to bind to ethylone and butylone as well as procaine, with the butylone pool capable of also binding to cocaine. Moreover, neither pool displayed any affinity for lidocaine. However, both pools did not demonstrate any binding towards α-PVP (FIGS. 2B and 3B), which indicated that the population of highly cross-reactive aptamers were relatively low. Meanwhile, the α-PVP pool showed no affinity for any of the targets or counter-targets (FIG. 4B).

Given that the α-PVP pool was not yet enriched, further rounds of selection were performed. From rounds six to eight, the same counter-target concentrations from round five was used with a further-reduced α-PVP concentration of 100 μM for positive selection. For the ninth round, the same α-PVP concentration was used but with 300 μM of each of the three aforementioned counter-targets. After the ninth round, the gel elution assay was performed with the enriched pool and a clear target-concentration-dependent elution profile was observed for α-PVP with an estimated dissociation constant ($K_D$) of 28 μM via fitting with the Langmuir equation (FIG. 5A). Notably, only 30% of the library was eluted, even in the presence of 1000 μM α-PVP, indicating that a small population of binders was enriched. The cross-reactivity and specificity of this enriched pool were also determined and the pool displayed affinity to ethylone and butylone, but was less response towards any other interferents (FIG. 5B), which can be attributed to the fact that more rounds of counter-SELEX was performed. Given that the pools enriched with individual targets also cross-reacted to other targets, it is possible that those pools contained highly cross-reactive aptamers.

Serial selection was then performed to enrich cross-reactive aptamers and exclude aptamers specific to individual targets. Specifically, 100 pmole of each enriched pool obtained from parallel selection were combined and the resulting combined pool was used as the new library. One cycle of serial selection was first performed, wherein the combined pool was challenged with each target one-by-one for a total of three rounds. For each round of the first cycle, counter-SELEX was initially performed using 500 μM each of cocaine, procaine, and lidocaine sequentially and then performed positive selection with 100 μM of either butylone (round 1), ethylone (round 2), or α-PVP (round 3). After this cycle of serial selection, a gel elution assay was performed to determine the cross-reactivity and specificity of the resulting pool (FIG. 6).

Results show that the cross-reactivity towards ethylone and butylone substantially increased ($K_D$=82 μM and 77 μM, respectively) relative to the respective individual pools at the end of parallel selection, while affinity towards α-PVP was similar ($K_D$=34 μM) (FIG. 6A). The specificity of the pool was high, with minimal affinity towards cocaine and lidocaine and a moderate response (30% cross-reactivity) to procaine (FIG. 6B).

Another cycle of serial selection was further performed with an identical selection procedure but with twice the concentration of the original counter-targets and additional counter-targets including 500 μM each of ephedrine, pseudoephedrine, acetaminophen, methamphetamine, and promazine. After this cycle, the pool binding affinity was evaluated via the gel elution assay (FIG. 7). More than 70% of the pool can be eluted by 500 μM of each individual target. The pool affinity towards ethylone and butylone increased by approximately 10-fold ($K_D$=6.9 μM and 9.5 μM, respectively), but the affinity towards a-PVP only marginally increased ($K_D$=21 μM) (FIG. 7A). At this stage this enriched-pool mostly consisted of cross-reactive aptamers binding to the core-structure shared by all synthetic cathinones.

Figure 8A:
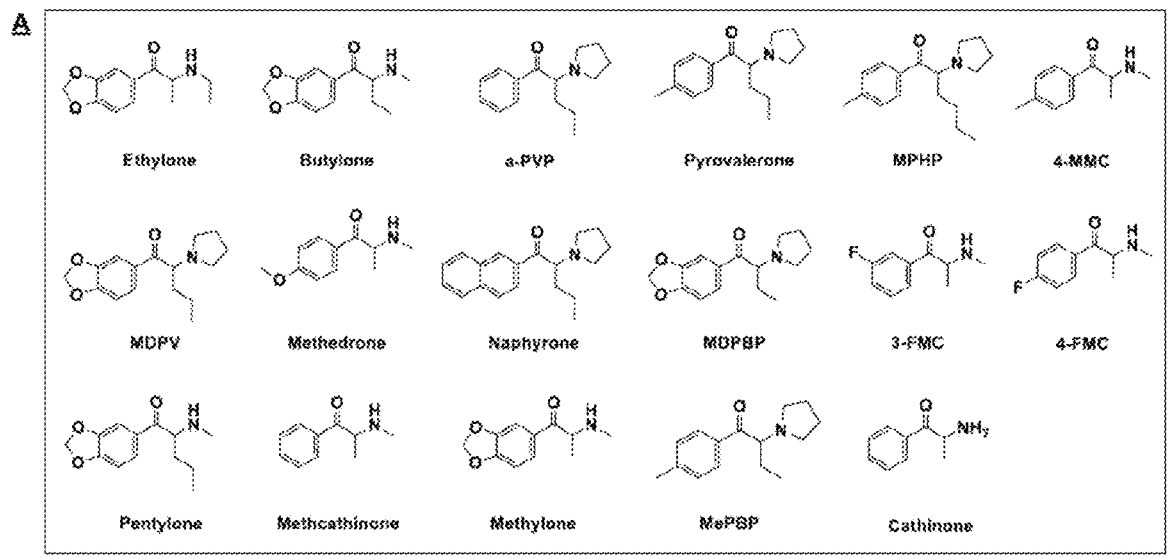

To confirm this, the gel elution assay was used to test the target-cross-reactivity of the final enriched pool by challenging it with the original three targets as well as 13 different synthetic cathinones (pyrovalerone, MPHP, 4-MMC, MDPV, methedrone, naphyrone, MDPBP, 3-FMC, 4-FMC, pentylone, methcathinone, methylone, and MEPHP) (Chemical structures see FIG. 8A). Of these targets, 14 synthetic cathinones demonstrated target-elution higher than 60% at a concentration of 50 μM, while the other two β-FMC and methcathinone) showed less elution but were still significantly higher compared to buffer alone (FIG. 7B). This result showed that the aptamer was capable of recognizing the core structure of synthetic cathinones, while even being tolerant to side-chain substituents that were not encountered during SELEX.

To evaluate the target specificity of the enriched pool, the pool was challenged with 50 μM of the counter targets (Chemical structures see FIG. 8B) and none of them showed specifically enhanced elution compared with buffer alone (FIG. 7B). Therefore, the final enriched pool was cloned and sequenced. The diversity of enriched pool was low, with 30 of the 50 clones having an identical sequence (FIG. 9). This consensus sequence was identified as a synthetic-cathinone-binding aptamer termed SCA2.1 (SEQ ID NO: 6). SCA2.1 has a stem-loop structure with a 9-base-pair stem and a 28-nucleotide loop under the selection buffer conditions at room temperature (FIG. 10). The target-binding affinity of this aptamer to the selection targets was then characterized using isothermal titration calorimetry (ITC). Specifically, a 300 μM solution of target was titrated into a 20 μM solution of the aptamer, recorded the heat released by each titration, and integrated the heats to generate a binding curve. Binding constants were determined using a single-site model and similar target-binding affinities ($K_D$) of 2.0 μM, 1.1 μM, and 3.1 μM and binding stoichiometries (N) of 1.6, 1.2, 1.7 were obtained for butylone, ethylone, and α-PVP, respectively (FIG. 11). These results not only demonstrate the high cross-reactivity of the aptamer, but also show that the binding mechanism may not be explained by a single-site model. Given the appearance of a two-phase binding modality, the aptamer may have a preference for one enantiomeric forms of targets.

Example 2—Naked-Eye Detection of Synthetic Cathinones

SCA2.1 was then used for sensitive, colorimetric detection of synthetic cathinones via a diethylthiotricarbocyanine (Cy7)-displacement assay. Cy7 is a small-molecule dye that exists in equilibrium between monomer and dinner forms, which have absorbance peaks at 760 nm and 670 nm, respectively. Previous studies have shown that Cy7 monomer can bind into hydrophobic target-binding domains of aptamers, which results in a significant enhancement of absorbance at 760 nm. The binding of target to the aptamer can displace Cy7 monomer from the binding domain within seconds, which causes the dye to dimerize in aqueous solution. This results in the reduction of absorbance at 760 nm and enhancement of absorbance at 670 nm, which enables Cy7 to be used as a colorimetric indicator for small molecule detection. (FIG. 12A). Such an assay can be employed to detect synthetic cathinones using SCA2.1.

Specifically, the binding affinity of Cy7 to SCA2.1 was determined by titrating different concentrations of the aptamer to 2 μM Cy7 (FIG. 13). Increasing the amount of aptamer progressively enhanced the absorbance of Cy7 monomer at approximately 760 nm, which indicated binding of Cy7 to the aptamer (FIG. 13A). A gradual peak shift from 760 nm to 775 nm was also observed, which is consistent with previous studies that showed that absorbance of the monomer can change in different microenvironments, such as when the dye binds to the aptamer. Using Cy7 absorbance at 775 nm, a $K_D$ of 1.6 μM was obtained (FIG. 13B).

Figure 14A:
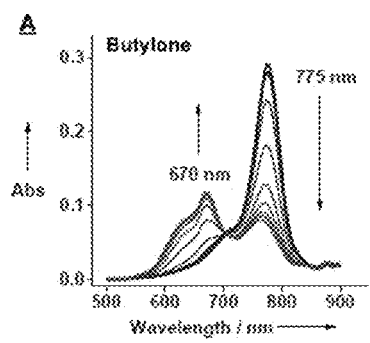
FIGS. 14A-14C show Cy7-displacement colorimetric assay for the detection of synthetic cathinones using SCA2.1. Absorbance spectra of Cy7 (2 µM) in the presence of varying concentrations (0, 0.1, 0.3, 0.5, 1.1, 2.3, 4.9, 10.3, 21.6, 45.4, 95.2, 200 µM) of (14A) butylone, (14B) ethylone, (14C) α-PVP, with the black-to-red color gradient representing increasing concentrations of synthetic cathinone target. [SCA2.1]=3 µM.
Figure 14B:
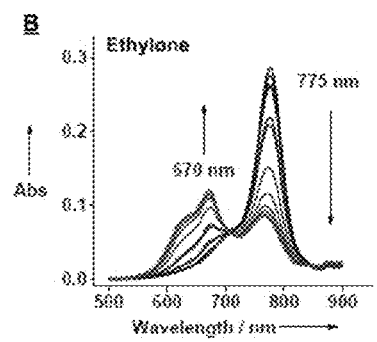
Figure 14C:
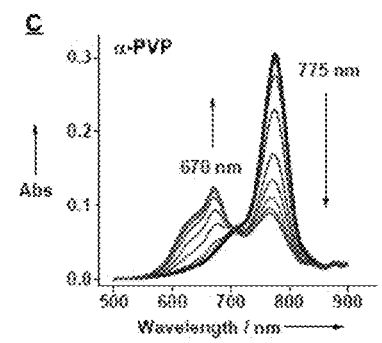
Figure 15A:
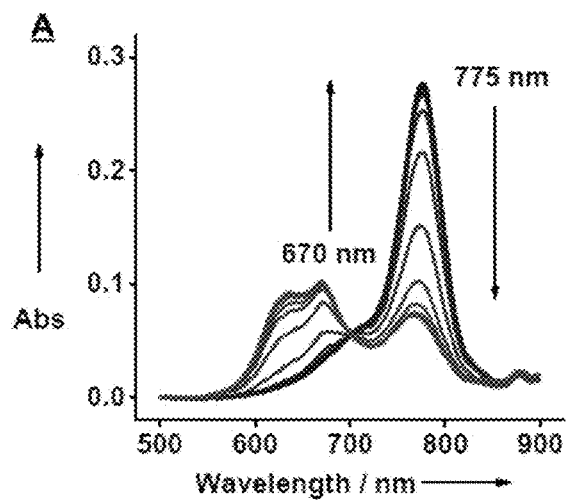
FIGS. 15A-15B show the detection of ethylone in 50% urine using the SCA2.1-based Cy7-displacement colorimetric assay. (15A) Absorbance spectra of Cy7 (2 µM) in the presence of varying concentrations of ethylone (0, 0.03, 0.06, 0.12, 0.25, 0.53, 1.11, 2.33, 4.90, 10.28, 21.60, 45.35, 95.24, 200 µM), with the black-to-red color gradient representing increasing concentrations of synthetic cathinone target. (15B) Assay calibration curve generated using 0-200 µM ethylone with the inset representing linear range from 0 to 1.2 µM target. [SCA2.1]=3 µM.
Figure 15B:
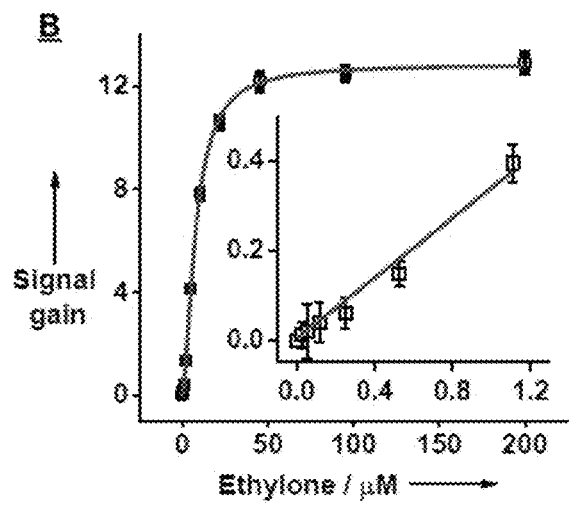

Whether the synthetic cathinone targets can efficiently displace Cy7 from SCA2.1 was then investigated. Different concentrations of butylone were first titrated into a mixture of 2 μM Cy7 and 3 μM SCA2.1, and increasing concentrations of butylone progressively reduced the absorbance of Cy7 at 775 nm while enhancing the absorbance at 670 nm (FIG. 14A). This change in the absorbance spectra of the dye can be attributed to dimerization of Cy7 monomer when displaced from the aptamer into solution. Based on the absorbance ratio between 670 nm and 775 nm ($A_{670}/A_{775}$), signal gain was calculated to generate a calibration curve displaying a linear range of 0-10 µM and a measurable detection limit of 200 nM (FIG. 12B). The same experiment was further performed using ethylone and α-PVP and similar spectral changes (FIGS. 14B and C), calibration curves, linear ranges, and detection limits (FIG. 12B) were obtained, indicating the high cross-reactivity of SCA2.1. The Cy7-displacement assay is also compatible with biosamples such as urine and saliva, since the absorbance range of Cy7 is far from the background absorbance regions of these matrices. Calibration curves were obtained using ethylone as target spiked in 50% urine (FIG. 15) and 50% saliva (FIG. 16) with a linear range of 0-10 µM and a measurable detection limit of 60 nM and 120 nM, respectively.

The enhanced sensitivity of the assay in these biomatrices can be possibly attributed to the higher ionic strength of the media, which may enhance target-binding to the aptamer or Cy7 dimerization. This assay is useful for label-free detection of synthetic cathinones in urine and saliva.

The cross-reactivity of the Cy7-displacement assay was further tested for nine other synthetic cathinones including naphyrone, MDPV, pentylone, methylone, 4-MMC, 4-FMC, 3-FMC, methcathinone and cathinone at a concentration of 50 µM. Despite the diversity of the side chains substituents, all synthetic cathinones induced a significant signal change in $A_{670}/A_{775}$ (FIG. 17A). Moreover, the aptamer-based assay exhibited high cross-reactivity to all tested synthetic cathinones, ranging from 50% to 150% relative to α-PVP (FIG. 17A). This implies that SCA2.1 mainly recognizes the beta-keto phenethylamine core structure, and variations in the side chains do not significantly affect target-binding affinity. Importantly, the assay has excellent specificity, as the aptamer does not cross-react to non-synthetic cathinone interferents. The Cy7 displacement assay was used to test 12 structurally-similar and -dissimilar interferent compounds including common illicit drugs (amphetamine, methamphetamine and cocaine) and cutting agents found in street samples (pseudoephedrine, ephedrine, procaine, lidocaine, benzocaine, caffeine, acetaminophen and sucrose) at a concentration of 50 µM. Despite many of the interferents containing a partial beta-keto phenethylamine structure, the assay yielded no response to them (FIG. 17A), indicating the high specificity of the aptamer.

The broad cross-reactivity of SCA2.1 to the synthetic cathinone family and its high specificity against interferent compounds makes this aptamer highly favorable for on-site drug screening. Therefore, the Cy7-displacement assay was fine-tuned for label-free synthetic cathinone detection by using a higher concentration of the dye and aptamer to intensify the target-induced color change for naked-eye observation.

This assay was challenged with the aforementioned 12 synthetic cathinone targets and 11 interferent compounds at a concentration of 50 µM with 3.5 µM Cy7 and 5 µM SCA2.1. In the absence of target, the aptamer-bound Cy7 monomer has an absorption peak at 775 nm which is not in the visible range, and thus the sample is practically colorless. However, in the presence of a synthetic cathinone, Cy7 is displaced by the target, which causes the Cy7 monomer to dimerize. The Cy7 dimer has an absorption peak at 670 nm, which makes the solution appear as a bright blue color that can be easily observed by the naked-eye (FIG. 17B). All synthetic cathinones induced a clear-to-blue color change in the solution within seconds, while no color change was identified upon addition of the interferent compounds (FIG. 17B). This result clearly demonstrated the feasibility of the Cy7-displacement assay for instrument-free on-site drug screening applications.

Figure 18:
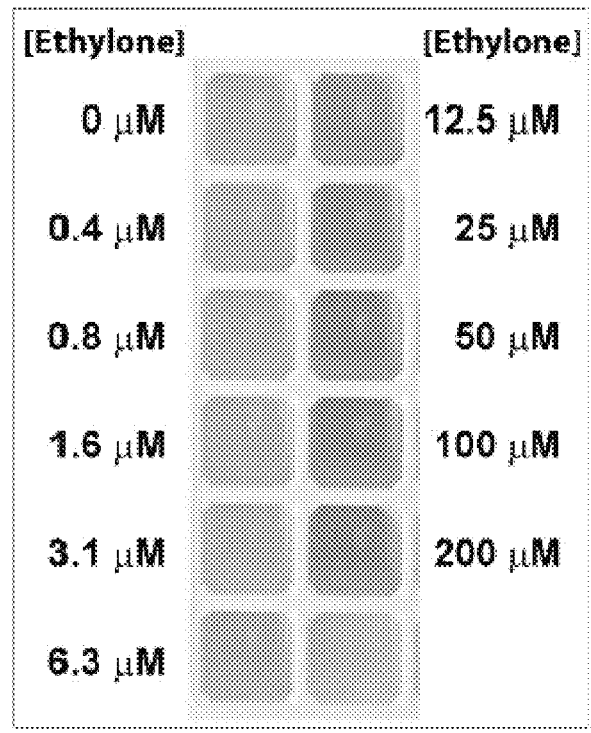
FIG. 18 shows the calibration curve of naked-eye detection of ethylone in the concentration range of 0.4 µM to 200 µM. The blue color change can be clearly observed with the ethylone concentration above 6.3 µM.

Calibration curve of naked-eye detection of ethylone in the concentration range of 0.4 µM to 200 µM was obtained (FIG. 18). The blue color change can be clearly observed by naked-eye with the ethylone concentration above 6.3 µM.

Example 3—Generating Structure-Switching Cross-Reactive Aptamers

Figures 19A, 19B, 19C:
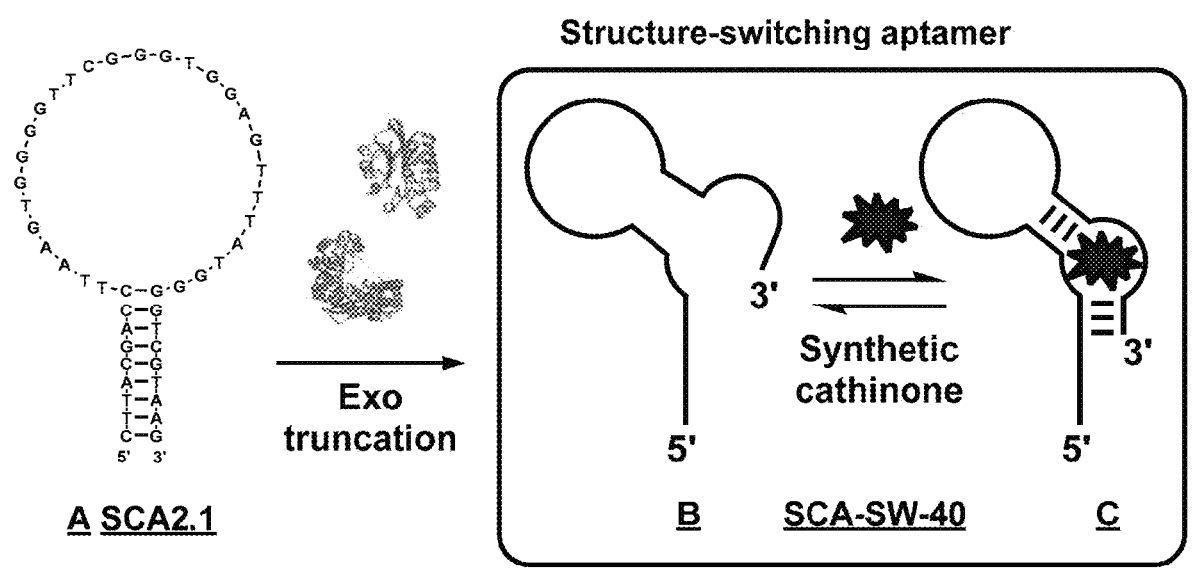
FIGS. 19A-19C show the exonuclease-mediated truncation of a synthetic-cathinone-binding aptamer to generate a structure-switching aptamer. (19A) SCA2.1 (SEQ ID NO: 6) possesses a fully folded stem. Exonuclease-mediated truncation of SCA2.1 generates a (19B) structure-switching aptamer (SCA-SW-40, SEQ ID NO: 18) which exists in an unfolded single-stranded state in the absence of target, but (19C) folds into a double-stranded structure in the presence of synthetic cathinones.

SCA2.1 adopts a fully folded structure in the absence of target (FIG. 19A). Structure-switching aptamers, which undergo a target-induced conformational change upon binding, can be readily adopted into various aptamer-based sensor platforms. To successfully transform the isolated cross-reactive aptamer into a structure-switching aptamer, an exonuclease-assisted truncation method is used. This strategy involves the removal of six nucleotides from the 3'-end of SCA2.1 to generate a structure-switching aptamer SCA-SW-40 (SEQ ID NO: 18) that remains in a single-stranded state in the absence of target (FIG. 19B), but folds into a double-stranded structure in the presence of synthetic cathinone drugs (FIG. 19C).

Example 4—Electrochemical Detection of Synthetic Cathinones

To perform rapid, sensitive, and interference-free electrochemical detection of synthetic cathinones in seized substances, the structure-switching synthetic-cathinone binding aptamer, SCA-SW-40 (SEQ ID NO: 18), was adopted into an electrochemical aptamer-based (E-AB) sensing platform.

Seized substances contain various impurities and/or adulterants. This is problematic for common on-site drug screening methods as these interfering molecules produce their own colored products in chemical spot tests and generate their own Raman spectra that overlap with the target spectra when performing Raman spectrometry. This causes drug-related signals to be masked by interfering molecules, resulting in inconclusive results.

E-AB sensors are an ideal choice for the detection of seized substances, because they are insensitive to sample matrix effects. Common drug impurities and adulterants do not produce an electrochemical signal at the typically-employed voltage. Additionally, E-AB sensors have rapid response times (seconds-scale), can perform detection with minimal sample preparation requirements, and can be easily miniaturized to detect low-volume samples (microliters), thus allowing for analysis of trace amounts of substances.

E-AB sensing utilizes surface immobilized aptamers to achieve sensitive and specific analyte detection. The signaling ability of an E-AB sensor is based on target-induced conformational changes in the electrode-bound, redox-labeled aptamer. Target binding changes the conformation of the aptamer, modifying the electron transfer efficiency between the redox reporter and the electrode surface.

Figures 20A, 20B, 20C:
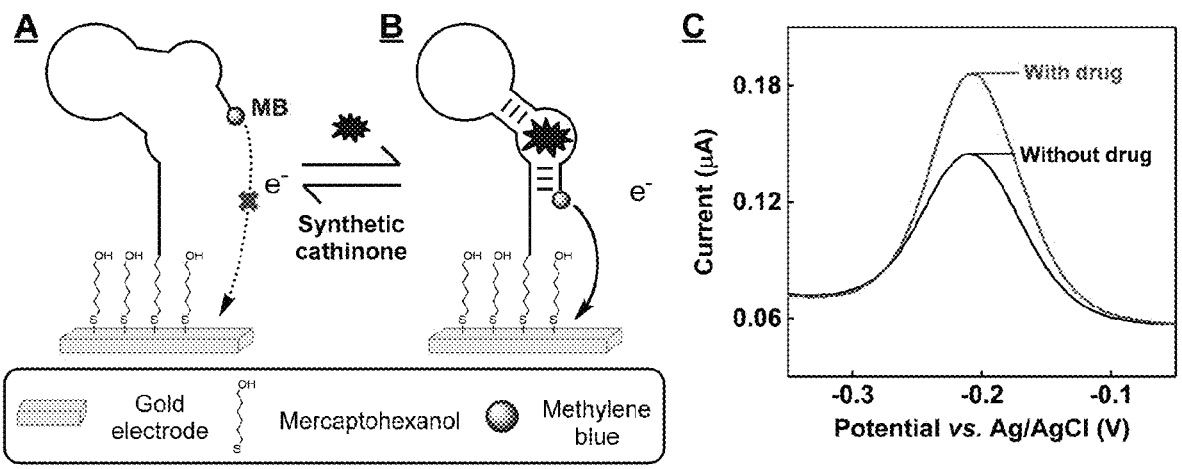
FIGS. 20A-20C show the electrochemical aptamer-based sensing of synthetic cathinone drugs. The structure-switching aptamer SCA-SW-40 is modified with a 6-carbon linker and a thiol group at its 5'-end, and a methylene blue redox tag at its 3'-end, respectively. (20A) In the absence of target the immobilized aptamer remains in a single-stranded flexible state, orientating the redox tag away from the gold surface which results in a small background current. (20B) In the presence of a synthetic cathinone drug, the aptamer binds to the target, transitioning to a double-stranded, folded structure which brings the redox tag close to the electrode surface, (20C) resulting in a large current increase.

To perform E-AB sensing, SCA-SW-40 was synthesized with a 5' thiol group (e.g., via a 6-carbon linker) and a 3' methylene blue redox tag (e.g., via a 7-carbon linker). The aptamers were immobilized onto the gold electrode surface via thiol-gold chemistry and backfilled using MCH to fill vacant areas on the electrode surface. In the absence of target, SCA-SW-40 exists in an unfolded state, lifting the redox tag away from the electrode surface and minimizing electron transfer (FIG. 20A). The presence of a synthetic cathinone drug induces a conformational change that brings the redox reporter close to the electrode surface (FIG. 20B), resulting in greater electron transfer efficiency, and ultimately a large current increase (FIG. 20C).

Figures 21A, 21B, 21C:
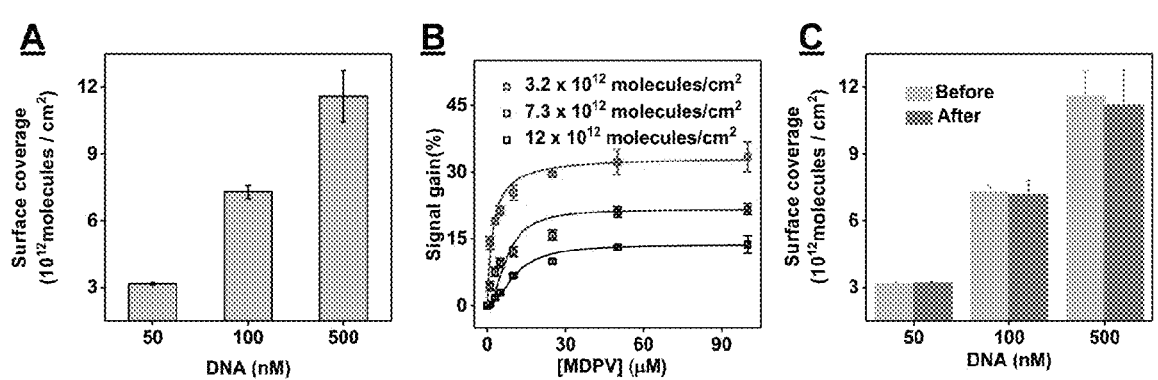
FIGS. 21A-21C show the effect of SCA-SW-40 surface coverage on E-AB sensor performance. (21A) The surface coverage of immobilized SCA-SW-40 for each electrode was measured using chronocoulometry. (21B) MDPV calibration curve was generated for each electrode (with differing SCA-SW-40 surface coverages) with a measurement frequency of 150 Hz. (21C) The stability of SCA-SW-40 monolayer on each electrode was measured before and after 50 scans. Error bars shown are standard error for the mean of measurements using three separate electrodes. Experiments were performed in selection buffer (10 mM Tris-HCl (pH 7.4), 20 mM NaCl, 0.5 mM $MgCl_2$).

SCA-SW-40-modified gold electrodes were prepared in the following way. SCA-SW-40 (in disulfide form) was incubated with tris(2-carboxyethyl)phosphine to reduce the 5' disulfide bonds. The thiolated aptamer (50, 100, or 500 nM aptamer) was incubated with a gold electrode (diameter=3 mm) overnight and then backfilled with 3 mM MCH. The surface coverage of immobilized SCA-SW-40 was found to be 3.2, 7.3, or $12\times10^{12}$ molecules/cm$^2$ for electrodes modified with 50, 100, or 500 nM SCA-SW-40, respectively (FIG. 21A). Calibration curves were generated using methylenedioxypyrovalerone (MDPV) as a model synthetic cathinone target (FIG. 21B). Measurements were performed in the original selection buffer (10 mM Tris-HCl (pH 7.4), 20 mM NaCl, 0.5 mM MgCl$_2$). Results show that electrodes modified with a lower surface coverage of SCA-SW-40 had higher sensitivity, with the electrode having a surface coverage of $3.2\times10^{12}$ molecules/cm$^2$ producing the highest signal gain (FIG. 21B). Additionally, the stability of the SCA-SW-40 monolayer was measured after 50 consecutive scans. Under all conditions tested, the electrodes were highly stable with little change in surface coverage (FIG. 21C), demonstrating the capability of E-AB sensing for reusable detection of synthetic cathinone drugs.

Example 5—Effect of Salt Concentrations on Synthetic Cathinone Detection

Figure 22A:
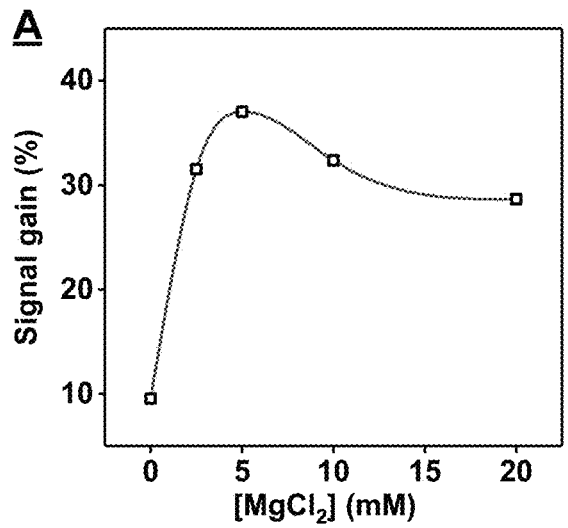
FIGS. 22A-22B show the optimization of $MgCl_2$ and NaCl in E-AB sensor buffer. (22A) Detection of 30 µM MDPV was performed under various $MgCl_2$ concentrations in the absence of NaCl. (22B) Detection of 30 µM MDPV was then performed using the optimized $MgCl_2$ concentration with various concentrations of NaCl. (Surface coverage=$1.5\times10^{12}$ molecules/$cm^2$).
Figure 22B:
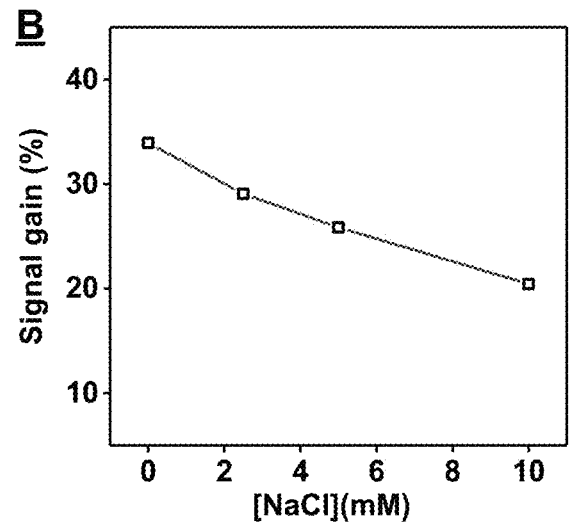

To optimize the concentrations of MgCl$_2$ and NaCl for improved signal gain, detection of 30 µM MDPV was first performed in the presence of various concentrations of MgCl$_2$ without any NaCl (FIG. 22A). 5 mM MgCl$_2$ was found to give the highest signal gain and was chosen for further NaCl optimization. Increasing the NaCl concentration resulted in a reduction of signal gain (FIG. 22B), as such 10 mM Tris-HCl (pH 7.4) and 5 mM MgCl$_2$ was determined to be the optimal buffer conditions for MDPV detection and were therefore used for all subsequent experiments unless otherwise specified.

Example 6—Effect of E-AB Surface Coverage on Synthetic Cathinone Detection

Figure 23A:
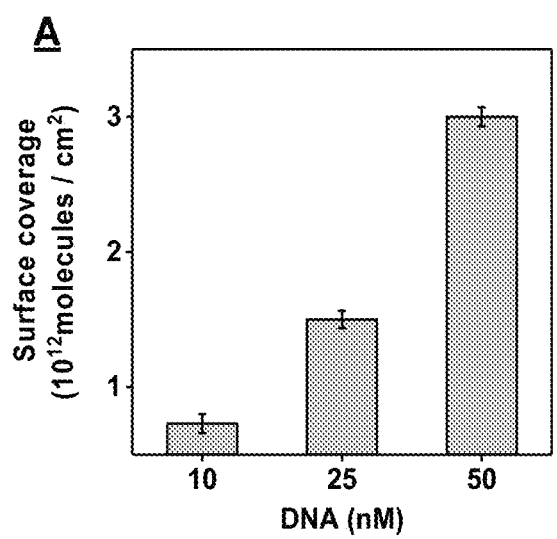
FIGS. 23A-23B show the optimization of SCA-SW-40 surface coverage for enhanced E-AB performance. Gold electrodes were modified with varying concentrations of SCA-SW-40 (10, 25, or 50 nM). (23A) The surface coverage of immobilized SCA-SW-40 was measured using chronocoulometry. (23B) A MDPV calibration curve was generated for each electrode with a measurement frequency of 150 Hz. Error bars shown standard errors for the mean of measurements using three separate electrodes. Experiments were performed using the optimized E-AB sensor buffer (10 mM Tris-HCl (pH 7.4), 5 mM $MgCl_2$).
Figure 23B:
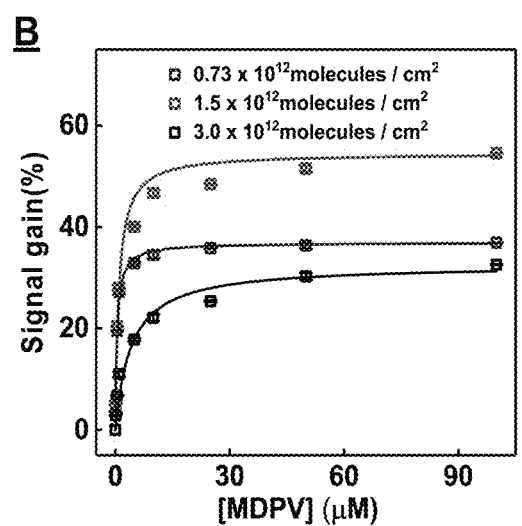

Results demonstrated that lower SCA-SW-40 surface coverage results in higher sensitivity (FIG. 21). The surface coverage was further reduced to achieve improved E-AB sensor performance. Gold electrodes were incubated overnight with either 10, 25, or 50 nM SCA-SW-40, producing surface densities of 0.73, 1.5, or $3.0\times10^{12}$ molecules/cm$^2$, respectively (FIG. 23A). MDPV calibration curves were generated for each electrode and an optimal surface coverage of $1.5\times10^{12}$ molecules/cm$^2$ were observed (FIG. 23B).

Example 7—Effect of Backfillers on Synthetic Cathinone Detection

Figures 24A, 24B:
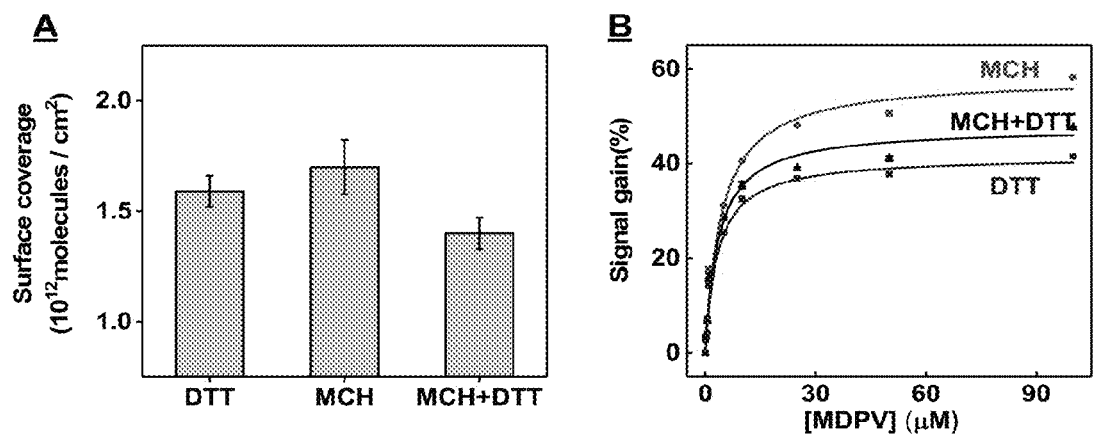
FIGS. 24A-24B show the effect of backfilling on E-AB sensor performance. (24A) Gold electrodes were modified with 25 nM SCA-SW-40 and backfilled using 3 mM dithiothreitol (DTT), 3 mM 6-mercapto-1-hexanol (MCH), or a combination of 1.5 mM DTT and 1.5 mM MCH. (24B) MDPV calibration curves for each electrode backfilled with either DTT, MCH or a combination of DTT and MCH, with a measurement frequency of 150 Hz. Error bars shown are standard error for the mean of measurements using three separate electrodes. Experiments were performed using the optimized E-AB sensor buffer (10 mM Tris-HCl (pH 7.4), 5 mM $MgCl_2$).

To further improve the sensor performance, the effect of different backfillers on sensitivity was studied. After modifying the electrode with 25 nM SCA-SW-40, the electrode was backfilled with either 3 mM DTT, 3 mM MCH, or a combination of 1.5 mM DTT and 1.5 mM MCH. Backfilling with various chemicals resulted in similar surface coverages for each electrode (FIG. 24A). MDPV calibration curves were subsequently generated for each electrode and observed the highest signal gain when only MCH was used (FIG. 24B).

Example 8—Effect of Distance Between the Redox Tag and Electrode on Synthetic Cathinone Detection Optimization of DNA surface coverage, electrolyte concentration, and backfiller achieve a maximal signal gain of 58% at a concentration of 100 µM MDPV. Specifically, SCA-SW-40 possesses a 5'-overhang that separates the redox tag and electrode by a large distance, thereby possibly limiting electron transfer efficiency upon target binding. Therefore, the removal of the 5'-overhang may improve sensitivity as the methylene blue tag will be orientated closer to the electrode surface in the presence of target, facilitating efficient electron transfer. Thus, the 5'-overhang of SCA-SW-40 was truncated to produce SCA-SW-34 (SEQ ID NO: 19) (FIG. 25A) and the sensitivity of the resulting aptamer-modified electrode was determined.

Figures 25A, 25B, 25C:
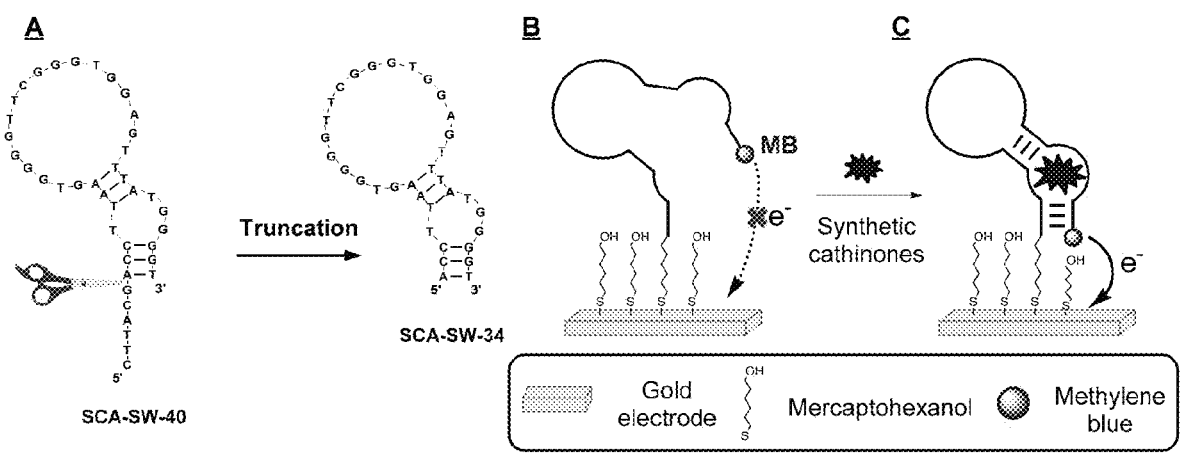
FIGS. 25A-25C show E-AB detection using 5'-3'-tandem-truncated aptamer. (25A) Manual truncation of the 5'-overhang of SCA-SW-40 (SEQ ID NO: 18) to produce SCA-SW-34 (SEQ ID NO: 19). (25B) SCA-SW-34 is modified with a 6-carbon linker and a thiol group at its 5'-end, and a methylene blue redox tag at its 3'-end, respectively. The immobilized aptamer remains in a single-stranded flexible state in the absence of target, orientating the methylene blue redox tag away from the gold surface. (25C) In the presence of a synthetic cathinone drug, SCA-SW-34 undergoes a target-induced conformational change into a double-stranded structure which brings the redox tag close to the electrode surface, resulting in an increase in current.

SCA-SW-34 was synthesized with a 5'-thiol (e.g., via a 6-carbon linker) and a 3' methylene blue redox tag (e.g., via a 7-carbon linker) and immobilized onto a gold electrode surface. Like SCA-SW-40, SCA-SW-34 remains unfolded in the absence of target, orientating the methylene blue redox tag away from the electrode surface (FIG. 25B). Upon target binding, SCA-SW-34 undergoes a target-induced conformational change, bringing the methylene blue tag close to the electrode surface and resulting in a large current increase (FIG. 25C).

The effect of the 5'-overhang of SCA-SW-40 on E-AB sensor performance was studied. Various concentrations of SCA-SW-34 or SCA-SW-40 were immobilized onto the gold electrode surface. The use of 25 or 50 nM of SCA-SW-34 or SCA-SW-40 produced similar surface coverages (FIG. 26A), indicating that the 5'-overhang has minimal effects on probe immobilization efficiency and surface coverage.

The sensitivity of each electrode was then tested for detection of 30 µM MDPV at various measurement frequencies (FIG. 26B). Under all applied conditions, SCA-SW-34 demonstrated greater sensor performance than SCA-SW-40 (FIG. 26B). The results demonstrated that lower SCA-SW-34 surface coverage leads to superior E-AB sensor performance with the greatest signal gain observed at $1.57\times10^{12}$ molecules/cm$^2$ (FIG. 26B). The experiment was repeated using lower concentrations of DNA for electrode modification (15 and 25 nM). Similarly, the use of 15 or 25 nM of SCA-SW-34 or SCA-SW-40 produced similar surface coverages (FIG. 27A), with the lowest surface coverage of SCA-SW-34 ($1.02\times10^{12}$ molecules/cm$^2$) having the highest signal gain (FIG. 27B). Despite a measurement frequency of 300 Hz providing the greatest signal gain, a frequency of 200 Hz was chosen for all subsequent experiments, as 300 Hz may destabilize the SCA-SW-34 monolayer.

Example 9—Effect of Buffer Conditions on the Sensitivity of the E-AB Sensor

To improve the sensitivity of the E-AB sensor even further, the buffer conditions were optimized for MDPV detection. Na$^+$ and Mg$^{2+}$ are cations that bind to DNA through electrostatic interactions with the negatively-charged phosphate backbone. This minimizes negative repulsive forces and aids in aptamer folding and target binding. Increasing the concentration of both these ions may improve aptamer affinity for MDPV, allowing for higher sensitivity. However, this may also stabilize the DNA structure in the absence of target, resulting in increased background signal. Thus, an optimal concentration of $Na^+$ and $Mg^{2+}$ that allows for high affinity with minimum background would be preferable.

The concentrations of NaCl and $MgCl_2$ in the ranges of 0-5 mM NaCl and 0-1 mM $MgCl_2$ were then optimized. A NaCl concentration of 0.1 mM and a $MgCl_2$ concentration of 0.03 mM was found to provide optimal sensor performance. A calibration curve was generated for MDPV detection using the optimized conditions. Results show that increasing concentrations of MDPV resulted in an increase in current (FIG. 28A). A detection limit of 100 nM MDPV was obtained for MDPV under the final optimized conditions (FIG. 28B).

Example 10—Cross-Reactivity and Specificity of the E-AB Sensor

The cross-reactivity of the E-AB sensor was assessed by challenging the sensor with 25 µM of various synthetic cathinones (α-PVP, ethylone, butylone, naphyrone, MDPV, pentylone, methylone, 4-MMC, 4-FMC, cathinone, 3-FMC, and methcathinone) in the optimized detection buffer. MDPV and pentylone yielded the highest signal gain at approximately 75% and 70% signal gain, respectively. Of the twelve synthetic cathinones, 8 of them (α-PVP, ethylone, butylone, naphyrone, MDPV, pentylone, methylone, and 4-MMC) yielded a signal gain above 45%. The other four synthetic cathinones (4-FMC, cathinone, 3-FMC, methcathinone) produced signal gains between 20-25% (FIG. 29). These results demonstrate that the E-AB sensor has excellent cross-reactivity to multiple members of the synthetic cathinone family.

Figure 30:
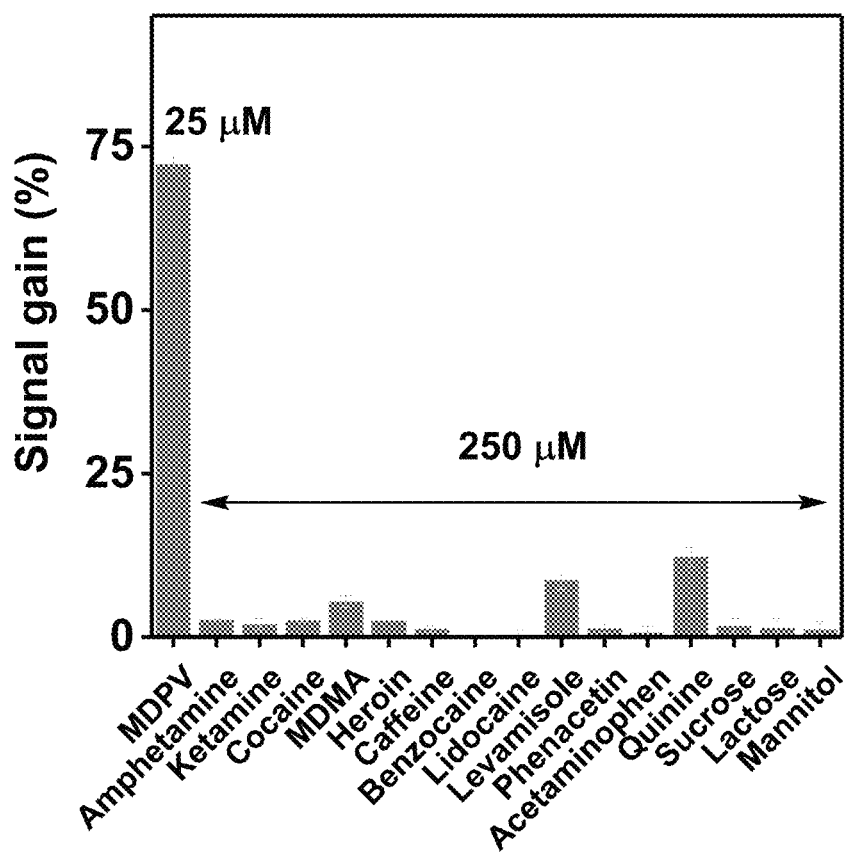
FIG. 30 shows the specificity of the E-AB sensor against various interferents at a concentration of 250 µM under optimized buffer conditions.

To test the specificity of the E-AB sensor, the sensor was challenged with interferent molecules including amphetamine (AMP), ketamine (KET), cocaine (COC), methylenedioxymethamphetamine (MDMA), heroin (HER), caffeine (CAF), benzocaine (BEN), lidocaine (LIDO), levamisole (LEV), phenacetin (PHE), acetaminophen (ACM), quinine (QUI), sucrose (SUC), lactose (LAC), and mannitol (MAN) (FIG. 30). All interferent molecules were tested at a concentration of 250 µM, and 25 µM MDPV was used as a positive control. All but two interferents produced a minimal signal gain (<5% signal gain) in comparison to a 10-fold lower MDPV concentration that produced a 75% signal gain. Levamisole and quinine produced signal gains of 10% and 15%, respectively, which is nonetheless still adequate for cathinone detection given that the purity of such drugs in seized samples range between 10-99%. These results demonstrate the specificity of the E-AB sensor against non-cathinone illicit drugs as well as common cutting agents and adulterants found in seized substances.

---

We claim:

1. An aptamer-based sensor comprising a cross-reactive aptamer for synthetic cathinones, the cross-reactive aptamer comprising SEQ ID NO: 16 or a sequence sharing at least 95% identity with SEQ ID No: 16.

2. The aptamer-based sensor according to claim 1, the cross-reactive aptamer being modified with a reporter label selected from a fluorescent dye, a fluorescent or luminescent nanoparticle, and an affinity tag.

3. An aptamer-based sensor comprising a cross-reactive aptamer for synthetic cathinones, the cross-reactive aptamer comprising SEQ ID NO: 15 or a sequence sharing at least 95% identity with SEQ ID No: 15.

4. The aptamer-based sensor according to claim 3, the cross-reactive aptamer being modified with a reporter label selected from a fluorescent dye, a fluorescent or luminescent nanoparticle, and an affinity tag.

5. The aptamer-based sensor according to claim 1, the synthetic cathinone having a core structure of

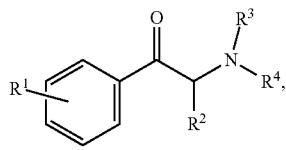

wherein $R^1$ is selected from the group consisting of hydrogen, alkyl, aryl, heteroaryl, cycloalkyl, cycloalkenyl, heterocycloalkyl, alkenyl, alkynyl, alkoxy, haloalkyl, acyl, halogen, and hydroxylalkyl, or $R^1$, taken together with the carbon atom to which it is attached and an adjacent carbon atom, form a substituted or unsubstituted 5- or 6-membered homocyclic or heterocyclic ring;

$R^2$ is hydrogen or alkyl; and $R^3$ and $R^4$ are each independently selected from the group consisting of hydrogen, alkyl, aryl, heteroaryl, cycloalkyl, cycloalkenyl, heterocycloalkyl, alkenyl, alkynyl, haloalkyl, acyl, halogen, and hydroxylalkyl, or $R^3$ and $R^4$, taken together with the nitrogen atom to which they are attached, form a substituted or unsubstituted 5- or 6-membered heterocyclic ring.

6. The aptamer-based sensor according to claim 5, the synthetic cathinone being selected from 3,4-methylenedioxypyrovalerone (MDPV); α-PVP; pyrovalerone; methylone; pentylone; 3,4-methylenedioxy-α-pyrrolidinobutiophenone (MDPBP); mephedrone; 4-methyl-α-pyrrolidinobutiophenone (MPBP); 4'-methyl-α-pyrrolidinohexanophenone (MPHP); naphyrone; methedrone; ethylone; butylone; 4-methylmethcathinone (4-MMC); 4-fluoromethcathinone (4-FMC); 3-FMC; methcathinone; and 4-methyl-α-pyrrolidinobutiophenone (MEPBP).

7. A method for detecting a synthetic cathinone in a sample, the method comprising contacting the sample with the aptamer-based sensor of claim 1, the aptamer-based sensor further comprising a dye, and detecting the presence of the synthetic cathinone in the sample by a signal generated upon binding of the synthetic cathinone to the aptamer.

8. The method according to claim 7, the dye being Cy7.

9. The method according to claim 7, the sample being a biological sample or an environmental sample.

10. The method according to claim 9, the biological sample being selected from blood, plasma, urine, tears, sweat, and saliva.

11. The method according to claim 7, wherein the signal generated upon binding of the synthetic cathinone to the aptamer can be observed by the naked-eye.

12. The method according to claim 7, the synthetic cathinone having a core structure of

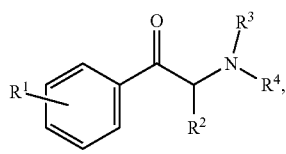

wherein $R^1$ is selected from the group consisting of hydrogen, alkyl, aryl, heteroaryl, cycloalkyl, cycloalkenyl, heterocycloalkyl, alkenyl, alkynyl, alkoxy, haloalkyl, acyl, halogen, and hydroxylalkyl, or $R^1$, taken together with the carbon atom to which it is attached and an adjacent carbon atom, form a substituted or unsubstituted 5- or 6-membered homocyclic or heterocyclic ring;
$R^2$ is hydrogen or alkyl; and
$R^3$ and $R^4$ are each independently selected from the group consisting of hydrogen, alkyl, aryl, heteroaryl, cycloalkyl, cycloalkenyl, heterocycloalkyl, alkenyl, alkynyl, haloalkyl, acyl, halogen, and hydroxylalkyl, or $R^3$ and $R^4$, taken together with the nitrogen atom to which they are attached, form a substituted or unsubstituted 5- or 6-membered heterocyclic ring.

13. The method according to claim 12, the synthetic cathinones being selected from MDPV; α-PVP; pyrovalerone; methylone; pentylone; MDPBP; mephedrone; MPBP; MPHP; naphyrone; methedrone; ethylone; butylone; 4-MMC; 4-FMC; 3-FMC; methcathinone; and MEPBP.

14. A method for detecting one or more synthetic cathinones in a sample, the method comprising contacting the sample with the aptamer-based sensor of claim 1, the aptamer-based sensor further comprising a dye, and detecting one or more synthetic cathinones in the sample by determining if a color change occurs, a change in color being indicative of the presence of one or more synthetic cathinones in the sample.

15. The method according to claim 14, the one or more synthetic cathinones being selected from MDPV; α-PVP; pyrovalerone; methylone; pentylone; MDPBP; mephedrone; MPBP; MPHP; naphyrone; methedrone; ethylone; butylone; 4-MMC; 4-FMC; 3-FMC; methcathinone; and MEPBP.

16. A method for detecting a synthetic cathinone in a sample, the method comprising contacting the sample with the aptamer-based sensor of claim 3, the aptamer-based sensor further comprising a dye, and detecting the presence of the synthetic cathinone in the sample by a signal generated upon binding of the synthetic cathinone to the aptamer.

17. The method according to claim 16, the dye being Cy7.

18. The method according to claim 16, the sample being a biological sample or an environmental sample.

19. The method according to claim 18, the biological sample being selected from blood, plasma, urine, tears, sweat, and saliva.

20. The method according to claim 16, wherein the signal generated upon binding of the synthetic cathinone to the aptamer can be observed by the naked-eye.

* * * * *